(12) United States Patent
Tribelsky et al.

(10) Patent No.: US 7,683,344 B2
(45) Date of Patent: Mar. 23, 2010

(54) IN-LINE TREATMENT OF LIQUIDS AND GASES BY LIGHT IRRADIATION

(75) Inventors: Zamir Tribelsky, Mevaseret Tzion (IL); Ytzhak Rozenberg, Ramat Gan (IL); Uri Levy, Rehovot (IL); Joseph Rabani, Jerusalem (IL)

(73) Assignee: Atlantium Technologies Ltd., Beit-Shemesh (IL)

( * ) Notice: Subject to any disclaimer, the term of this patent is extended or adjusted under 35 U.S.C. 154(b) by 691 days.

(21) Appl. No.: 10/566,992

(22) PCT Filed: Aug. 4, 2004
(Under 37 CFR 1.47)

(86) PCT No.: PCT/IL2004/000717

§ 371 (c)(1),
(2), (4) Date: Jan. 4, 2007

(87) PCT Pub. No.: WO2005/011753

PCT Pub. Date: Feb. 10, 2005

(65) Prior Publication Data

US 2007/0272877 A1    Nov. 29, 2007

(30) Foreign Application Priority Data

Aug. 4, 2003    (IL) .................................. 157229

(51) Int. Cl.
*G01N 21/01*    (2006.01)
(52) U.S. Cl. .............. 250/435; 250/428; 250/432 R; 250/437; 210/748; 422/24
(58) Field of Classification Search ............ 250/428, 250/432 R, 435, 437; 422/24; 210/748
See application file for complete search history.

(56) References Cited

U.S. PATENT DOCUMENTS

| 4,296,066 A | 10/1981 | Schenck |
| 4,948,980 A | 8/1990 | Wedekamp |

(Continued)

FOREIGN PATENT DOCUMENTS

| DE | 41 10 687 | 10/1991 |
| JP | S55-124585 | 9/1980 |

(Continued)

OTHER PUBLICATIONS

International Search Report for Internation Application No. PCT/IL2004/000717, mailed on Nov. 19, 2006.

*Primary Examiner*—Jack I Berman
*Assistant Examiner*—Hanway Chang
(74) *Attorney, Agent, or Firm*—Pearl Cohen Zedek Latzer, LLP

(57) ABSTRACT

An in-line reactor for the treatment of liquids or gasses by light radiation is disclosed. The reactor is made of tube, pipe, or chamber made of a transparent material, having at least one fluid inlet and correspondingly at least one fluid outlet. The transparent material of the tube is selected such that its refractive index is as possible close to the refractive index of the fluid to be treated. Air gap is kept around the outer transparent walls of the reactor, in order to allow for total internal reflection inside the reactor, of light directed into it from a light source in angles of incidence greater than the critical angle. Fluid treatment systems comprising at least one said in-line reactor are also disclosed. Furthermore, method of in-line fluid treatment, and especially of water sterilization and disinfection and aseptic filling of water are disclosed. Surfaces hit by the in-line disinfected water after being launched through an outlet nozzle, could also be sterilized by launching the water with the same UV light used for the in-line treatment locked in total internal reflection within the free flow water jet.

21 Claims, 16 Drawing Sheets

U.S. PATENT DOCUMENTS

| | | | |
|---|---|---|---|
| 5,200,156 | A | 4/1993 | Wedekamp |
| 5,413,768 | A | 5/1995 | Stanley, Jr. |
| 5,685,980 | A | 11/1997 | Patapoff et al. |
| 5,832,361 | A * | 11/1998 | Foret .................. 422/186 |
| 5,874,741 | A | 2/1999 | Matschke |
| 6,055,085 | A | 4/2000 | Nakashima et al. |
| 6,086,760 | A | 7/2000 | Hoffa |
| 6,323,601 | B1 | 11/2001 | Klein et al. |
| 6,454,937 | B1 | 9/2002 | Horton et al. |
| 6,707,048 | B2 * | 3/2004 | Hallett et al. ............. 250/431 |
| 6,773,608 | B1 | 8/2004 | Hallett et al. |
| 6,902,654 | B2 | 6/2005 | Michishita et al. |
| 6,932,903 | B2 * | 8/2005 | Chang .................. 210/192 |
| 7,002,140 | B2 | 2/2006 | Elsegood et al. |
| 7,604,773 | B2 | 10/2009 | Ekstrom et al. |
| 2003/0155524 | A1 * | 8/2003 | McDonald et al. ......... 250/435 |
| 2004/0036034 | A1 | 2/2004 | Hur et al. |

FOREIGN PATENT DOCUMENTS

| | | |
|---|---|---|
| JP | S63-302940 | 12/1988 |
| JP | H11180733 | 7/1999 |
| JP | 2000-15090 | 1/2000 |
| JP | 2001-204439 | 7/2001 |
| JP | 2002-93712 | 3/2002 |
| JP | 2002-1757111 | 6/2002 |
| JP | 2002/262837 U | 9/2002 |
| JP | 2003-117432 | 4/2003 |
| JP | 2004-508893 | 3/2004 |
| JP | 2004-159710 | 6/2004 |
| JP | 2005-510415 | 4/2005 |
| WO | WO 01/98150 | 12/2001 |
| WO | WO 03/033413 | 4/2003 |
| WO | WO 03033413 A1 * | 4/2003 |

* cited by examiner

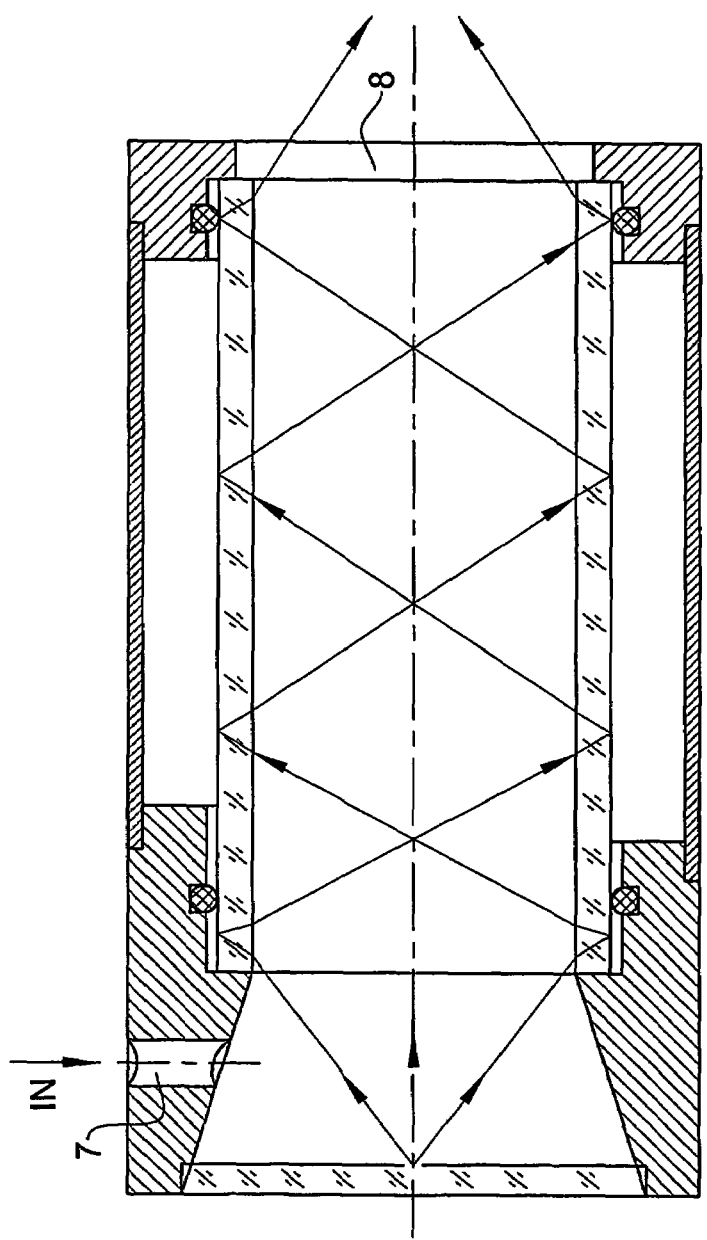
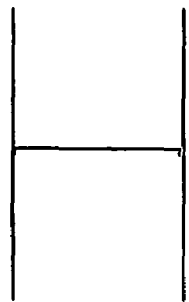
FIG. 5
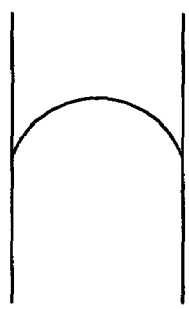
FIG. 4
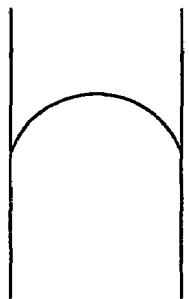
FIG. 3
FIG. 2

IN-LINE TREATMENT OF LIQUIDS AND GASES BY LIGHT IRRADIATION

CROSS-REFERENCE TO RELATED APPLICATIONS

This application is a National Phase Application of PCT International Application No. PCT/IL2004/000717, International Filing Date Aug. 4, 2004, claiming priority of IL Patent Application 157229, filed Aug. 4, 2003 the entire disclosures of both of which are incorporated herein by reference.

FIELD OF THE INVENTION

This invention relates to in-line irradiation of fluids, and more specifically to the treatment of liquids (especially water) and gases (especially air) on their way from a source to a destination by light radiation (especially in the UV range). Further more the present invention relates to disinfection of solid surfaces related to the in-line treatment of the liquids or gases.

BACKGROUND OF THE INVENTION

Water is a multi purpose life resource. It uses for drinking, cleaning, irrigation, swimming, and for very wide variety of industrial utilities including in the food industry. Due to the vitality of water for life, population development significantly influenced from the availability of water, and thus efforts are always made to increase water availability and to reduce the expenses involved in their production. This is because the existence of rich water sources not always assures their adaptation to the intended use, due to the presence of other substances in it. In many of water uses there exist standards and health requirements as for the quality of water with respect to the concentration of contaminants in it, which are no doubt essential, but normally increase the production costs of water due to special treatments it should have in order to bringing it with conformity with such standards and requirements. The costs of water treatment is often such high, such that pure populations cannot withstand, thus abandon themselves to the dangers hiding in non treated water. Furthermore, costs of water treatment many time prevent water recycling, and thus even in places all over the world were water is not so much available or low priced, water is wasted in huge amounts after single use, since their recycling treatment costs higher.

Although in pure populations the costs of water production are critical to people lives, they are also of highly significance in well developed populations as well, from several aspects. This is because water treatment costs very much influence life level indexes, since water is involved in all life aspects either directly (i.e. in direct consumption such as drinking, washing, swimming) and indirectly (i.e. in indirect consumption such as industrial processes).

The present invention shall concentrate on disinfection and decontamination of water from health damaging biological and chemical substances.

When dealing with water disinfection, it should always be remembered that in order to maintain the aseptic conditions of disinfected water, it is required that all the solids and gasses that may become in contact with such water should be disinfected as well then maintained in an appropriate aseptic condition.

During the years several basic concepts of disinfection and decontamination of water have been developed, which compete on the global market with their advantages and disadvantages.

Many times, producers harness several disinfection concepts on one production line, wherein, for example, water reservoirs and conveyor belts are decontaminated using toxic chemicals (then washed very strictly to avoid chemical residuals from the end product), water pipes are decontaminated by delivering boiled water, end product bottles are disinfected using chemicals, and the water itself (as a product) may be irradiated by UV light for disinfection.

It is appreciated that a most significant factor in determining what treatment concept would be chosen for a decontamination treatment, is the cost involved. Probably, chemical disinfection process which involves the use of toxic substances which should then be cleaned off and removed, will not be chosen unless other concepts, e.g. heating, costs higher.

Another clean disinfection concept which involves no toxic substances is irradiating the disinfected medium by germicidal UV light. However, although many patents have been issued and many efforts are all the time made to provide UV disinfection system having industrial capacity that may address all sorts of production requirements and still offer reasonable prices either for establishment and for current maintenance, a great success in that field could not yet be observed.

One obstacle in the path of providing optimal UV disinfection devices is the cost of the optics. Optic systems which will allow for a reliable disinfection process needs to ensure that each and every portion of the disinfectant will receive appropriate amount of germicidal energy. Unfortunately, the either the basic costs and the maintenance costs of such optical systems are not small enough so as one may absolutely prefer the UV concept versus others.

One obstacle in the path of providing optimal UV disinfection devices is the cost of the UV light source itself, and of course its maintenance costs.

U.S. Pat. No. 6,454,937 to Horton et. al. and U.S. Pat. No. 5,200,156 to Wedekamp, are both directed to irradiating flowing fluids with UV light in a direction along the flowing path, in order to maximize the efficiency of the UV energy and to minimize the absorption of UV light by the walls of vessels or pipes which contain the irradiated fluid. For this purpose UV light sources are arranged according to said patents to emit maximum energy in a direction parallel to the axis of a pipe (or pipes) through which flows the fluid.

SUMMARY OF THE INVENTION

The present invention relates to a reactor for the treatment of fluids with light radiation, comprising a tube or a vessel made of transparent material and surrounded by air, and having a fluid inlet, a fluid outlet, and at least one opening or window adapted for the transmission of light from an external light source into the tube.

According to various preferred embodiments of the present invention the tube or the vessel is made of quartz.

According to various preferred embodiments of the present invention the tube or the vessel is positioned inside a protective sleeve with an air gap in between.

According to various preferred embodiments of the present invention the window is provided with optical filter for avoiding light of unwanted wavelengths from entering the reactor.

According to various preferred embodiments of the present invention the reactor is further comprising light detectors in light communication with predetermined regions at an outer side of the tube or the vessel and in data communication with a controller of a disinfection system making use of the reactor.

According to additional embodiments of the present invention the reactor is further comprising at least one additional tube or vessel made of transparent material wherein the transparent tubes are of descending diameters and are positioned one inside another with gaps in between, about the same longitudinal axis, forming a multi core reactor.

According to other embodiments the reactor is further comprising at least one additional tube made of transparent material wherein the transparent tubes or vessels are of descending diameters and are positioned one inside another with gaps in between, about the same longitudinal axis, forming a multi core reactor.

According to various preferred embodiments the fluid outlet is formed as a filling nozzle in a liquid filling apparatus, or as a water launcher in a washing apparatus.

The present invention refers also to a disinfection device, comprising at least one reactor as defined by any of the previous claims, and at least one light radiation source aligned into the reactor.

The device according to the present invention may further comprise light detectors in light communication with predetermined regions of a transparent wall of a tube inside the reactor, and in data communication with a controller of the disinfection device.

The device of the present invention could be used in a domestic water supply system, and accordingly may further comprise a faucet adapted to be activated by a domestic user, in liquid communication with a fluid outlet of the reactor.

The device of the present invention could be used also in an air conditioning or circulating system, with its fluid inlet or outlet in air communication with at least one air blower or air pump.

According to various preferred embodiments the at least one light radiation source of the device of the present invention is selected from microwave excited electrodeless UV plasma lamp, UV laser, mercury lamp, spherical medium pressure UV lamp, or any other acceptable source of light.

The present invention further relate to a method for irradiating fluids, the method comprising accommodating fluid in a reactor, the walls of which are made of a transparent material, and the surrounding outside the wall is of a refractive index lower then that of the wall, and irradiating the accommodated fluid with light radiation aligned into the fluid in such an angle, such that light is transmitted through the fluid, and such that a major portion of light which leaves the fluid through its boundaries with the transparent wall is reflected back into the fluid or remains to shine along the transparent wall.

The method of the present invention refers either to operation modes wherein the fluid is in continuous flow during the irradiating process, as well as to operation modes wherein the fluid is held motionless for a predetermined time interval of the treatment.

According to various preferred embodiments of the invention the transparent material of the reactor is quartz.

According to various common uses of the method of the present invention, the fluid accommodated in the reactor is water or other liquid transparent to certain wave lengths of the light radiation.

According to various utilization ways of the method of the present invention the fluid accommodated in the reactor is water or other liquid transparent to certain wave lengths of the light radiation, and the method is further comprising launching the water from the outlet to form a free flow water jet with light radiation locked in total internal reflection within the jet.

The method of in-line disinfection according to the present invention may further comprising washing a surface or a container with the free flow jet, or filling a bottle or a container with the free flow jet. According to additional implementations of the method, it comprises filling a container with the free flow jet, and simultaneously evacuating the air rejected from the container by the liquid being filled, and suctioning it into a second reactor according to the present invention, or into a second flow channel in the same reactor in which the liquid is irradiated, for irradiating the air.

DETAILED DESCRIPTION OF THE INVENTION

The present invention relates to a method for irradiating fluids (mainly liquids, and most specifically water, however, as will be further explained, according to various embodiments air could be treated as well, and according to other embodiments portions of irradiation energy escaping the liquid flowing in one flow channel could be utilized for treatment of air in a separate flow channel), the method comprising accommodating (either in flow, otherwise immovably for a predetermined treatment time interval) liquid in a reactor (hereinafter will be referred to also as "tube", "vessel" or "pipeline") the walls of which are made of a transparent material preferably (in order to allow total internal reflection within a sufficiently wide range of angles of incidence of the light radiation) having a refractive index as close as possible to or lower than that of the liquid, and the surrounding outside the wall is of a refractive index lower then that of the transparent wall, and irradiating the accommodated liquid with light radiation aligned into the liquid in such an angle, such that light is transmitted through the liquid, and such that a major portion of light which leaves the liquid through its boundaries with the transparent wall is reflected back into the liquid (in most cases this reflection will preferably be designed as total internal reflection (TIR)) or remains to shine along the pipeline wall.

As will be further explained, light which remains trapped to shine inside the pipeline wall (due to total internal reflection between the wall boundaries with the water and between the wall boundaries with the air) could still be utilized when it exits through the pipeline edge. Furthermore and as will be explained in detail later on, light refracted out of the pipeline to the surrounding air, could still be utilized for irradiating the air.

It should be notified that method and devices for irradiation of liquids or of gases according to the present invention has mainly been developed by the inventors of the present invention for the purpose of disinfecting, decontaminating, sterilizing, or neutralizing hazardous biological or chemical substances that may exist in the liquids or gases to be treated. However, the present invention does not limit itself from other processes that could be carried out for the treatment of liquids or of gases using the method or the devices according to the present invention.

According to one preferred embodiment of the present invention, especially useful for irradiating water (having refractive index $N1=1.33$), the pipeline wall is made of quartz (having refractive index $N2=1.54$), and the surrounding is of air (having refractive index $N3=1.0003$).

The light energy is preferably directed into the liquid such that all light components will enter the liquid in angles greater then the critical angel for obtaining total internal reflection (TIR) of the light inside the liquid. However if so desired, it is possible to guide the light energy (or parts of it) in smaller angles in order to intentionally lose predetermined amounts of light energy, e.g. for irradiating the air around the pipeline or e.g. for having predetermined light energy emerging from the edge of the pipeline for irradiating a target opposite the edge.

Preferably, the quartz pipeline is placed inside a protective sleeve made of metal or of plastic, with an air gap in between. Spacers could be positioned near the ends of the pipeline or in predetermined intervals along its length in order to hold the pipeline with its longitudinal axis substantially overlapping that of the sleeve. The spacers could be made as integral protrusions protruding from the pipeline material, from the sleeve material, or from a separate material located or bonded between the sleeve and the pipeline, or a combination thereof.

According to various embodiments of the present invention, at least one light sensor is provided in the air gap between the sleeve and the pipeline for monitoring light characteristics. This could be helpful for obtaining real time information and using it as a feedback for controlling the light, or as an alarm for the water condition e.g. in washing water recycling system in a plant wherein a small amount of water is used according to the present invention for washing prefilled containers and is disinfected in-line according to the method of the present invention. The water could thus be recycled until the monitored intensity, of the irradiating energy is decreasing beyond a predetermine lower limit which notifies the system that water turbidity percentage prevents effective disinfection, so that the used water should be replaced by fresh, or alternatively, UV light intensity should be increased until it comply with the current water conditions (i.e. until the monitored intensity returns above a predetermined threshold).

It should be appreciated that due to the internal reflection phenomenon (and preferably total internal reflection), the pipeline according to the present invention is not limited to straight paths, and it could be designed in a non linear manner according to local requirements of a specific plant e.g. bottle filing plant, water purifying plant etc.).

It should further be appreciated that due to the internal reflection inside the pipeline, the average path length made by the entire light photons emitted by a light source during a given time interval, is greater according to the present invention in tens of percents comparing to the average path length made by a similar dose of light photons directed into conventional pipes of straight lines, e.g. of U.S. Pat. No. 6,454,937 to Horton et. al. and of U.S. Pat. No. 5,200,156 to Wedekamp. In these patents, a photon that finds its direction diagonally to the pipe axis is absorbed by the pipe wall, while in the pipeline according to the present invention it will be reflected back into the liquid, zigzagging through the water all along the pipeline length.

Due to the longer light path per a given length reactor, and due to the possibility to "fold" the reactor by bending it in spirals or in windings, the reactor according to the present invention may have more compact design and could be adapted more easily to different design requirements as may exist in various sites and production lines were the disinfection system should be installed.

It should be noted however that the greater the path of the light inside the water is, the greater the light efficiency is. This is because the probability of every photon to meet bacteria (or other toxic specie or chemical) along its way is increased as its path length in the water increases.

Therefore, according to various preferred embodiments of the present invention the pipeline length is extended intentionally (i.e. in addition to the inherent path extension of the light due to the internal reflection) as a part of the design, thus increasing the water path length and the average light path length inside, respectively. To this end, the pipeline could be provided in winding format, or in spiral shape that will allow accommodating a pipe of a relatively long length in a disinfection device of relatively small dimensions. Such increase in the light path length through the water is inapplicable in prior art systems, and as could be appreciated from U.S. Pat. No. 6,454,937 to Horton et. al. and of U.S. Pat. No. 5,200,156 to Wedekamp, the UV energy is designed to be completely absorbed in the water in straight pipe lines. As could be appreciated, prior art disinfection systems are limited of having the light radiation passing windings in the pipeline. Accordingly, UV energy distribution in prior art systems, is designed such that energy is distributed laterally. Although both U.S. Pat. No. 6,454,937 to Horton et. al. and U.S. Pat. No. 5,200,156 to Wedekamp, are directed to in-line disinfection, i.e. to light distribution along the path of flow, both involves parallel distribution of the energy. Horton uses an array of parallel pipes, while Wedekamp uses an array of UV light sources within a chamber of an increased diameter in a mid portion of the pipeline. Although the present invention does not restricts itself from using parallel geometries, its main approach, contrarily to prior art systems, is to concentrate large light power through the length of the pipelines, in order to distribute the energy to maximum possible extent. While in prior art system the implementation of such approach will involve great lose of energy that will be absorbed by pipeline walls, the present invention allows for using powerful light pulses of pick powers of several orders greater then in prior art systems and without lose of efficiency, because in the present invention the water path could be extended as much as required for absorbing the entire light energy in the water.

The use of burst pulses of UV light having extreme pick power is known in its significantly efficient bacteria killing, comparing to similar amounts of energy when distributed averagely (e.g. in CW, or in relatively wide pulses i.e. pulses lasting for more then several microseconds and having moderate pick power declining in water after several tens of centimeters of absorbance). According to the present invention extremely high pick power pulses could be utilized and be adapted to pass through respective long flow paths (without being absorbed and get lost inside the pipeline walls as occur in prior art devices), due to the light conductivity of pipeline wall according to the present invention and due to the total internal reflection that could be achieved by surrounding the transparent pipe lines with a gap of air.

The present invention further relates to new geometry of coupling UV light (especially of light sources emitting the light from longitudinal tubes, e.g. Microwave Excited UV-Lamps, or various types of mercury UV lamps) into pipelines for the purpose of in-line disinfection.

According to this new geometry the UV light tube is positioned with its axis parallel to a substantially straight window made in or being the wall of a junction between two ends of pipe segments oriented with an angle between them both, the angle is preferably as twice or more wider than the critical angle for total internal reflection in the pipe segments, such that the light emitted from a substantially one half of the UV light tube length enters the window and irradiating the water accommodated in one of the pipe segments while the light emitted from substantially the second half of the UV light tube length enters the window and irradiating the water accommodated in the second of the two pipe segments. The UV light tube is equipped with a reflector on its backside (the side of it which is opposite to the window) which is designed to reflect light emitted from the backside of the tube or light reflected back from the window, back into the two pipe segments. Each of the pipe segments could be of a length and of a path form according to particular design considerations differing from one case to another. For example the pipe segment could be extended in windings or in spiral configuration for a length appropriate to efficient utilization of the energy of a predetermined light tube. Each segment could also be connected at its opposite end in a similar manner to another pipe segment, with a similar substantially straight window in the junction there between, wherein another light tube (and accompanied reflector) could be positioned for dividing its illumination between the two light segments. As may be appreciated, this configuration could be extended like a chain of pipe segments wherein each two of which are interconnected in an appropriate angle and having a substantially straight window in the junction thereof, useful for receiving the light from the UV light tube, with total internal reflection inside each of the segments., This architecture is advantageous no only in that it allows to design in-line disinfection systems without limitations concerning the liquid path length, but also in that it facilitate the maintenance of such disinfection systems by allowing replacement of malfunctioning light radiation sources during the disinfection process, i.e. without stopping the flow of liquid. Furthermore, it allows for adapting the number of active light radiation sources on-real time basis, according to the flow rate in the pipeline.

The present invention further relates to in-line disinfection system of fluids (mainly liquids, and most specifically water, however, as will be further explained, portions of irradiation energy escaping the liquid could be utilized for treatment of air), comprising (a) at least one pipeline segment, the walls of which are made of a transparent material having a refractive index close to or lower than that of the liquid, and the surrounding outside the wall is of a refractive index lower then that of the wall; (b) light radiation source aligned into the liquid in such an angle, such that its light could be transmitted through the liquid, and such that a major portion of light which may leave the liquid through its boundaries with the pipeline wall is reflected back into the liquid (preferably in total internal reflection (TIR)) or remains to shine along the pipeline wall.

As will be further explained, light which remains trapped to shine inside the pipeline wall (due to total internal reflection between the wall boundaries with the water and between the wall boundaries with the air) could still be utilized when it exits through the pipeline edge. Furthermore and as will be explained in detail later on, light refracted out of the pipeline to the surrounding air, could still be utilized for irradiating the air.

According to one preferred embodiment of the present invention, especially useful for irradiating water (having refractive index $N1=1.33$), the pipeline wall is-made of quartz (having refractive index $N2=1.54$), and the surrounding is of air (having refractive index $N3=1.0003$).

Preferably, the quartz pipeline is placed inside a protective sleeve made of metal or of plastic, with an air gap in between. Spacers could be positioned near the ends of the pipeline or in predetermined intervals along its length in order to hold the pipeline with its longitudinal axis substantially overlapping that of the sleeve. The spacers could be made as integral protrusions protruding from the pipeline material, from the sleeve material, or from a separate material located or bonded between the sleeve and the pipeline, or a combination thereof.

According to various embodiments of the present invention, at least one light sensor is provided in the air gap between the sleeve and the pipeline for monitoring light characteristics. This could be helpful for obtaining real time information and using it as a feedback for controlling the light, or as an alarm for the water condition e.g. in washing water recycling system in a plant wherein a small amount of water is used according to the present invention for washing pre-filled containers and is disinfected in-line according to the method of the present invention. The water could thus be recycled until the monitored intensity of the irradiating energy is decreasing beyond a predetermine lower limit which notifies the system that water turbidity percentage prevents effective disinfection, so that the used water should be replaced by fresh, or alternatively, UV light intensity should be increased until it comply with the current water conditions i.e. until the monitored intensity returns above a predetermined threshold).

According to various embodiments of the present invention, the reactor is made multi-core, i.e. the path of the liquid is through at least two pipelines each is of a different diameter, all of which are arranged one inside another about a substantially one common imaginary axis in a descending diameters order, such that a plurality of separate flow channels are created each between two parallel neighboring pipelines.

BRIEF DESCRIPTION OF THE DRAWINGS

In order to understand the invention and to see how it may be carried out in practice, it will now be described, by way of non-limiting example only, with reference to the accompanying drawings, in which:

FIG. 2 illustrates the general optical path of light irradiated through the reactor of FIG. 1.

FIG. 3 illustrates in an approximated curve the energy distribution density in a reactor cross section.

FIG. 4 illustrates in an approximate curve the fluid flow distribution in a reactor cross section.

FIG. 5 illustrates in an approximate curve a superposition between the curves of FIG. 3 and FIG. 4.

DETAILED DESCRIPTION OF THE DRAWINGS

Figure 1:
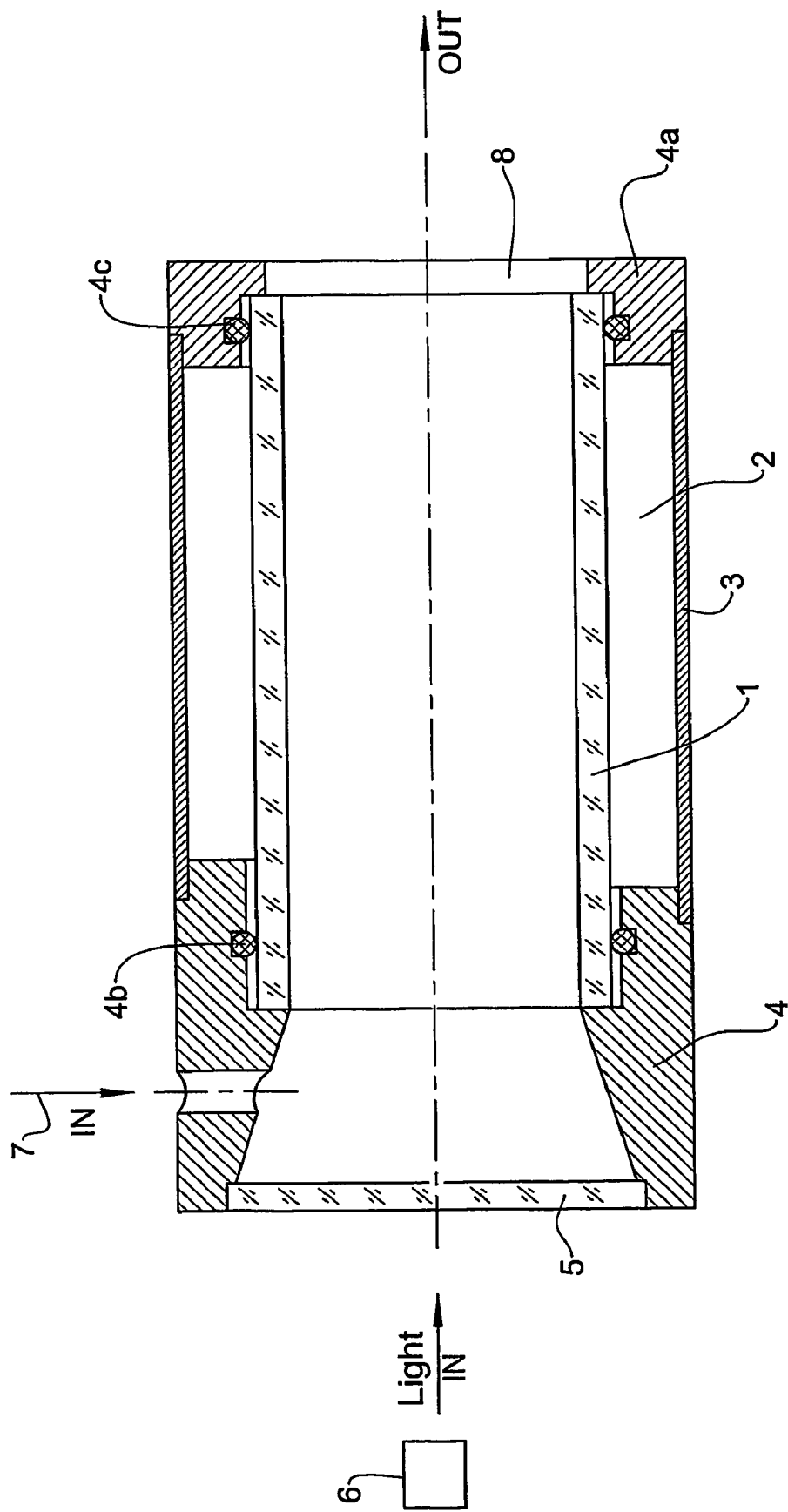
FIG. 1 illustrates a cross sectional view along a basic reactor according to the present invention.

FIG. 1 illustrates a cross sectional view along a basic reactor according to the present invention. The reactor may be used as a pipeline or as a portion of a pipeline, and is comprised of a quartz tube (1) located inside a protective metal sleeve (3) with an air gap (2) in between. The quartz tube (1) is connected on its first end to a first spacer (4) spacing between the metal sleeve (3) connected to one of its ends, and between the quartz tube (1). A second spacer (4a) is spacing between the next ends of the quartz tube and the protective sleeve. Gaskets (4b) and (4c) seals the connections between the quartz pipe ends and the respective spacers. The spacers could be made of metal, plastic, rubber, or any other acceptable material. They could also be produced from quartz. Accordingly they can form, if so wished, either an integral unit with the gaskets (e.g. in case both are rubber made), an integral unit with the quartz (e.g. in case both are quartz made), or an integral unit with the protective sleeve (in case both are made of the same material). The first spacer (4) serves also as light/fluid mixer unit. A fluid inlet (7) is made at the wall of the first spacer (4) through which fluid may enter and flow via quartz tube (1) to reach the outlet (8). The first spacer (4) has a transparent end (5) through which light may enter into the reactor. At least one UV light source (6) is positioned opposite the transparent end wall (5) of the first spacer (4), and it is preferably should be aligned so as to irradiate into the reactor light. rays in angles greater then that of the critical angle for obtaining total internal reflection inside the reactor. The transparent end wall (5) is illustrated as a flat surface, however it could be designed in any required form in order to allow alignment of light energy from light source (or a plurality of light sources) into the quartz tube (1) which alignment is in a desired angle for achieving predetermined internal reflection properties (in most cases total internal reflection will be preferred). For example, the transparent wall could be formed, concave, convex, conic, or other. Furthermore, it could be designed with special optical properties, e.g. as a lens cooperating with the light sources being aligned and or with reflector or reflectors of such light sources. Further more the transparency of the end wall (5) could be made selective, by making it as or by plating it with or by coupling to it a filter enabling the penetration of a selected range of wavelengths, or preventing penetration of selected wavelengths. For example, if the UV light source emits also radiation in the IR range, or emits UV in a specific undesired wavelength (e.g. UV wavelength which may cause ozonation of water molecules) the end wall could be provided with filtering means avoiding penetration of IR (or of undesired UV wavelength) into the reactor.

The scope of the present invention is not limited to any particular shape of the quartz tube or tubes. These could be designed to have plain cylindrical shape, or to have any other desired shape which does not unacceptably deteriorates its internal reflection properties. Accordingly, it may designed as to have (either in portions of it or in its entirety) a conical shape, an elliptical shape, a cubic shape, or combinations thereof.

FIG. 2 illustrates the general optical path of light irradiated through the reactor of FIG. 1. The arrows represent the zig-zagging path of light rays irradiating the fluid while being reflected from the quartz walls. Light rays exiting through the outlet (8) of the quartz tube continue their path through the liquid (in case the reactor is fed with liquid through the fluid inlet (7), then launched out through the outlet (8)) locked in total internal reflection inside the jet of liquid launched through the outlet, and follow its trajectory until it reaches its destination.

FIG. 3 illustrates in an approximated curve the energy distribution density in a reactor cross section. The dense of light rays in the middle of the quartz tube is greater than near the quartz wall, because through the middle come also light rays emitted directly from the light source (i.e. without first being reflected from the walls). The convexity of the illustrated curve at its mid portion is analogues to the higher density near the longitudinal axis of the quartz tube, and the inclination of the curve toward the left on its ends is analogues to the lower density of the light near the quartz wall.

FIG. 4 illustrates in an approximate curve the fluid flow distribution in a reactor cross section. Naturally, the flow speed of a fluid around the longitudinal axis of a pipeline is higher than near the pipeline walls. Therefore, greater volumes of fluid pass in the middle of a pipe then in its margins. The convexity of the illustrated curve at its mid portion is analogues to the greater fluid volumes passing near the longitudinal axis of the quartz tube, and the inclination of the curve toward the left on its ends is analogues to the fewer fluid, volumes passing near the quartz wall.

FIG. 5 illustrates in an approximate curve a superposition between the curves of FIG. 3 and FIG. 4. The curve is nearly a straight line which may represent the nearly uniform dose of light energy per unit volume of the fluid. This is to say that there is a compatibility between the distribution of the light energy and the distribution of the fluid rough the reactor according to the present invention, which helps in optimization of the energy amounts invested in the disinfection process.

Figure 6:
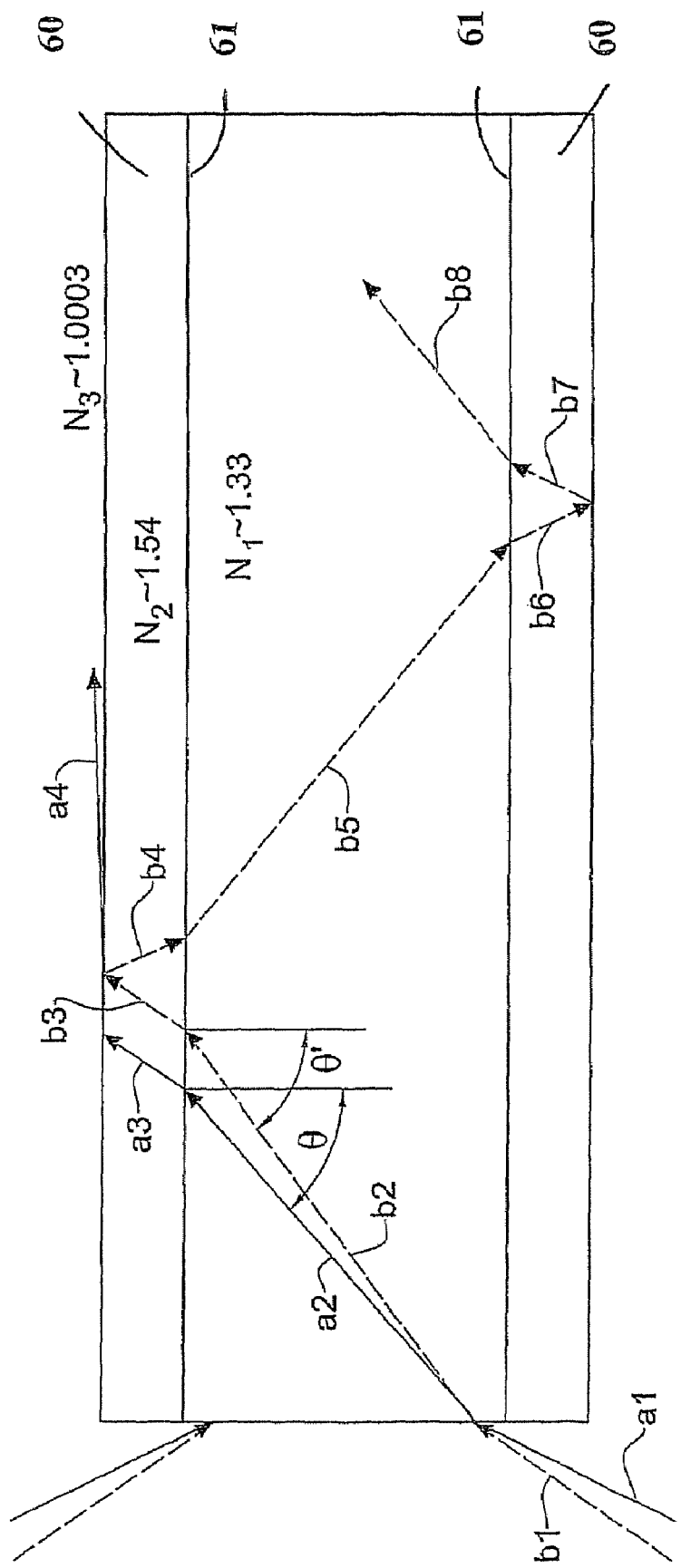
FIG. 6 illustrates in detail the optical paths of light through a quartz reactor according to the present invention.

FIG. 6 illustrates in detail the optical paths of light through a quartz reactor according to the present invention. The line comprised of arrows (a1), (a2), (a3) and (a4) represents a light ray aligned toward the reactor to hit the inner surface (61) of the quartz pipe in an angle of incidence equal to the critical angle marked $\ominus$. The segment (a4) of the ray represents lose of light energy refracted by the quartz wall (60) to the outer side of the reactor, nearly parallel to the wall. According to the present invention such lost light could still be utilized, e.g. for irradiating air evacuated from a container being filled by an in-line filler according to the present invention. However in embodiments of the present invention wherein there is no intention to lose light energy to the outer side of the quartz tube, the lose of energy could be minimized by aligning the light from the light source into the reactor such that it will hit the inner surface (61) of the quartz wall (60) in an angle of incidence $\ominus'$ greater than the critical angle $\ominus$. The line comprised of the arrows (b1), (b2), (b3), (b4), (b5), (b6), (b7), (b8)

represents light ray aligned to hit the inner surface (61) of the quartz wall (60) in an angle of incidence a little bit greater than the critical angle ⊖. As can be seen, this light ray is fully reflected (b4) from the quartz-air boundary it hits, back (b5) into the fluid, then (b6) to the quartz—air boundary on the opposite direction, and so on, zigzagging through the fluid, along the reactor. As can be seen in this figure, the pairs of arrow lines (a2) and (a3), as well as (b2) and (b3), (b5) and (b6), (b7) and (b8) are forming, each pair respectively, angles of spreading out from the inner side of the reactor into the quartz wall, an vice versa—angles of spreading out from the quartz wall into the inner side of the reactor. These angles of spreading are due to the higher refractive index of the quarts (N2–1.54) comparing to that of the fluid (N1=1.33 in case the fluid is water; N3=1.0003, in case the fluid is air), and they are greater in case the reactor is used for air treatment, which in turn result in larger critical angle (i.e. for achieving TIR in case the fluid flowing inside the container is air).

Figure 7:
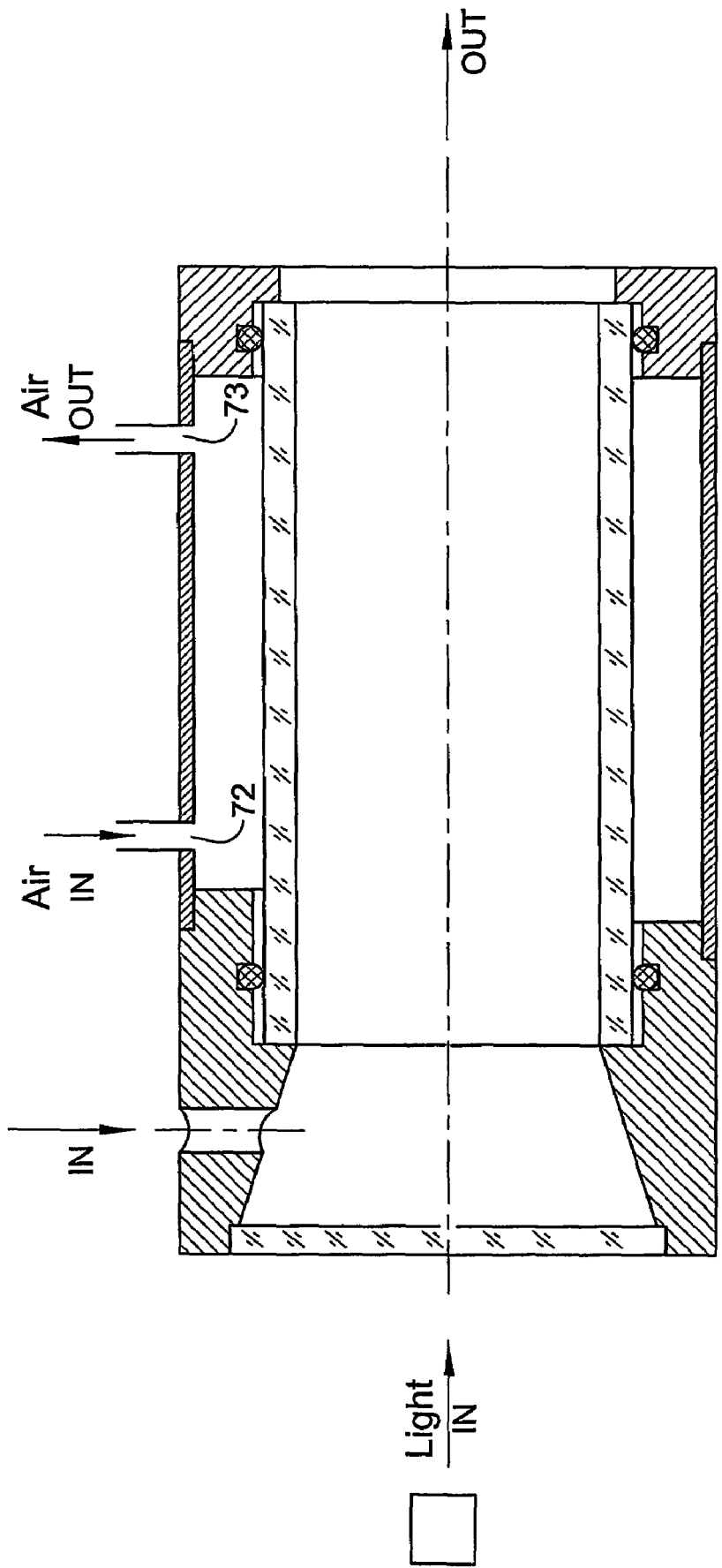
FIG. 7 illustrates a cross sectional view of a basic dual reactor intended to the treatment of liquid in a first flow path and of gas in a second flow path.

FIG. 7 illustrates a cross sectional view of a basic dual reactor intended to the treatment of liquid in a first flow path and of gas in a second flow path. Concerning the first flow path the description is similar to that given in FIG. 1, above. Concerning the second flow path, air inlet (72) and air outlet (73) are made in the metal protective sleeve, through which air could now be caused to flow, being irradiated by light rays refracted out of the quartz wall either intentionally, or as a lose of light energy in a non intentional manner.

Figure 8:
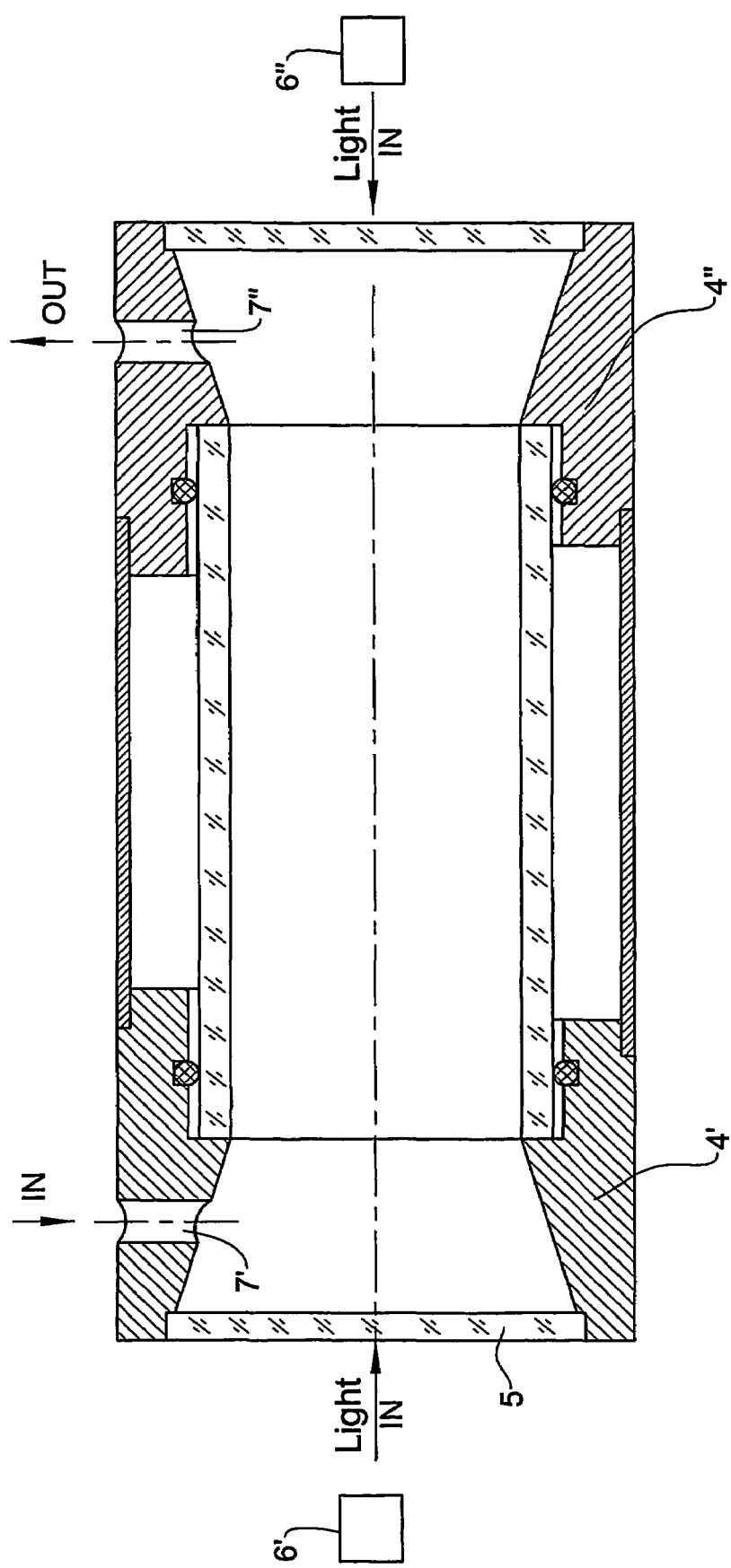
FIG. 8 illustrates a cross sectional view of a basic reactor having two light radiation sources operating in opposite directions.

FIG. 8 illustrates a cross sectional view of a basic reactor having two light radiation sources operating in opposite directions. This embodiment differs from that of FIG. 1 in that the reactor is comprised of two units (4') (4") of the spacer, which are connected respectively each on a different opposite end of the quartz tube, instead of spacer (4) and spacer (4a) connected on the quartz tube of FIG. 1. In this embodiment of FIG. 7, the spacer (4") on the right side of this figure, is utilized for exiting the fluid which has entered the reactor through the fluid inlet (7') of the left side spacer (4'). Accordingly, the inlet (7") of the spacer (4") is actually using in this present embodiment as a fluid outlet.

According to this embodiment the reactor could be irradiated by light sources (6') and (6"), from opposite directions. These light sources could be identical ones, or different ones, and they may be operated simultaneously, or separately, with correlation or without, all according to design considerations and according to disinfection process type.

Figure 9:
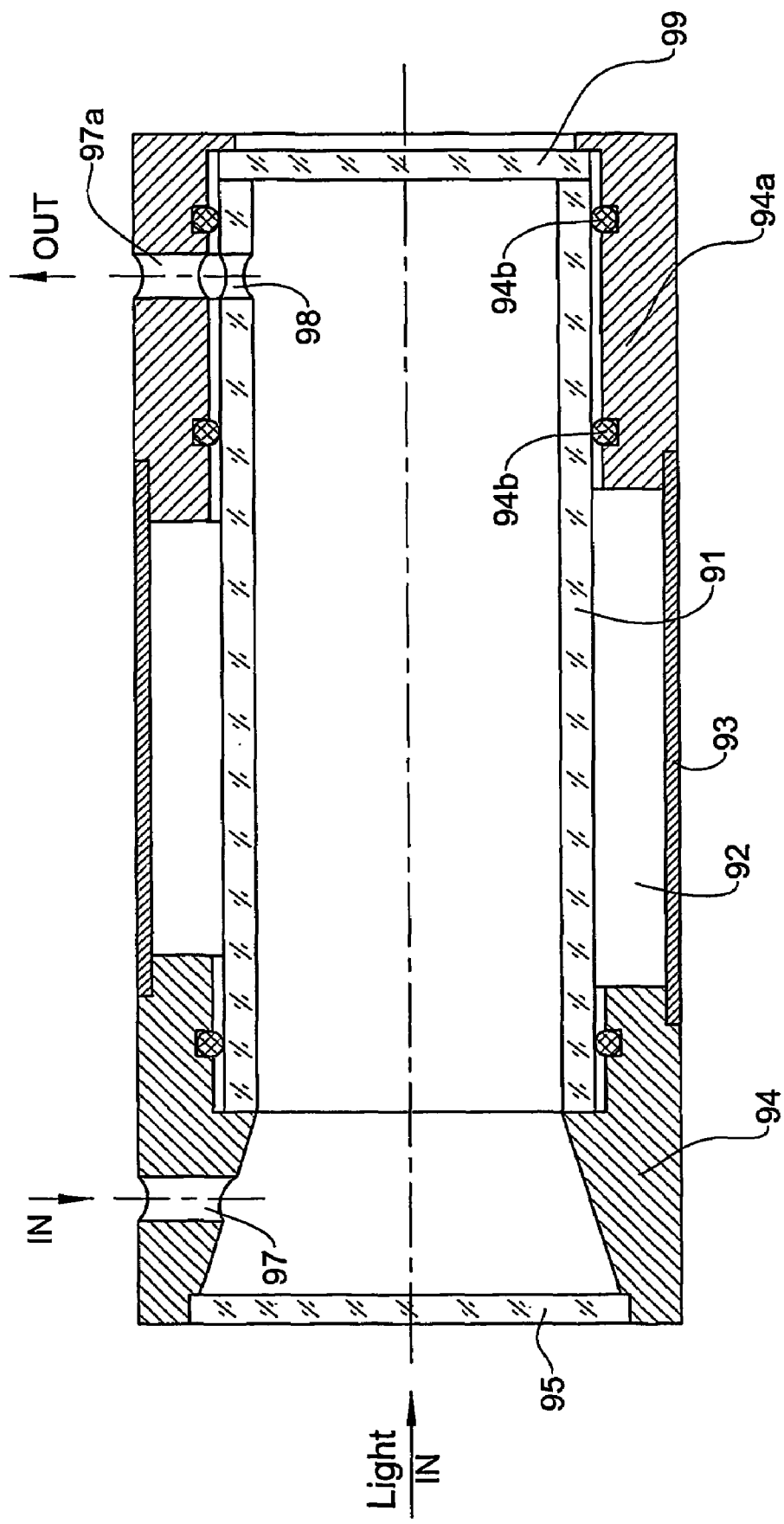
FIG. 9 illustrates a cross sectional view of a basic reactor having a back reflector.

FIG. 9 illustrates a cross sectional view of a basic reactor having a back reflector. The reactor according to this embodiment is comprised of a quartz tube (91) opened from its one end to which a spacer (94) is connected, and closed from its opposite end by means of a back reflector (99). Fluid may enter the quartz tube (91) through fluid inlet (97) made in the wall of the spacer (94), and exit quartz tube through opening (98) made in the quartz wall and is in fluid communication with fluid outlet (97a), made in the wall of a spacer (94a) connected on the closed end of the quartz tube (91). A metal protective sleeve (93) connected between the two spacers (94) and (94a), covers the quartz tube (91), with an air gap (92) in between. Gaskets (94b) seal the connections between the quartz tube (91) and the spacers (94) and (94a). Light directed in appropriate angles through the reactor transparent end (95) pass through the reactor either directly or be total internal reflection between the quartz walls, until it reaches the back reflector (99) and returns back through the reactor, in both paths (directly and through TIR).

Figure 10:
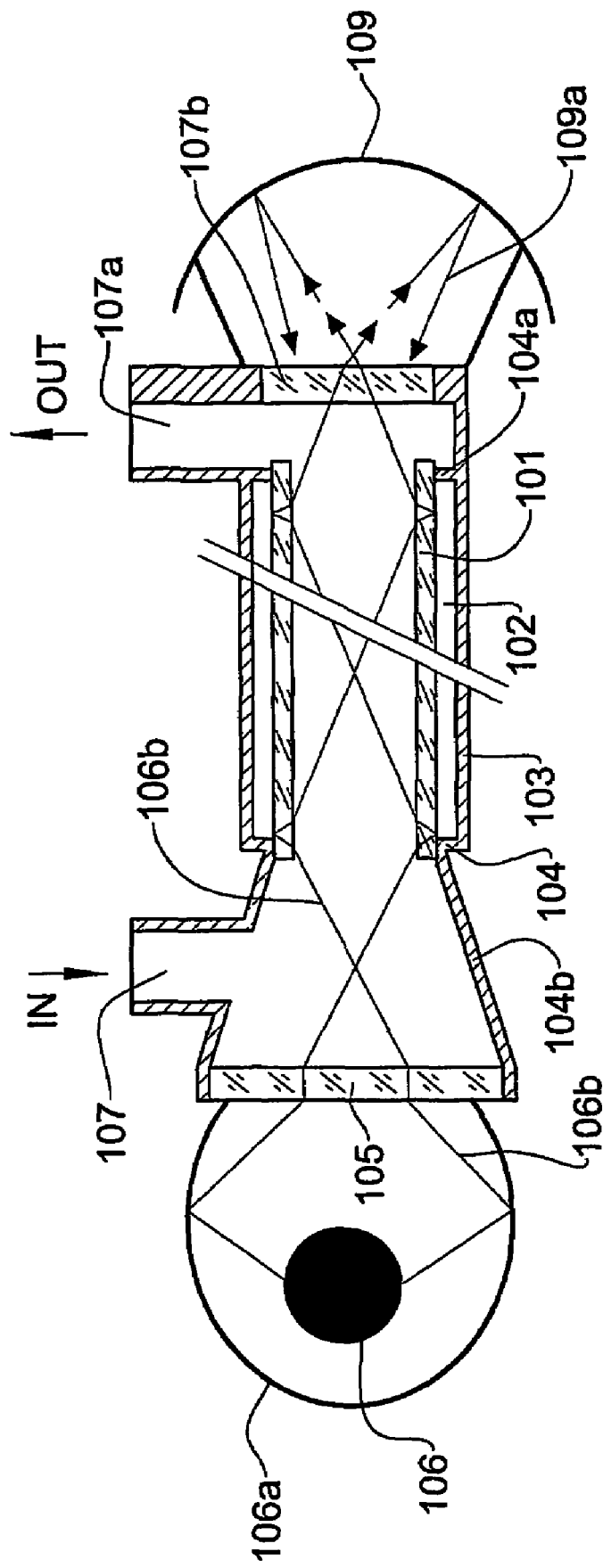
FIG. 10 illustrates a cross sectional view of another reactor embodiment according to the present invention, having a spherical medium-pressure UV lamp and a back reactor.

FIG. 10 illustrates a cross sectional view of another reactor embodiment according to the present invention, having a spherical medium-pressure UV lamp and a back reactor. The reactor is comprised of a quartz tube (101) located inside and spaced from a protective sleeve (103) with a gap of air (102) in between. The protective sleeve (103) and the quartz tube (101) are spaced from one another by spacers (104) and (104a). On its left hand the quartz tube (101) is opened to a light-fluid mixer unit (104b) having on its wall a fluid inlet (107). The mixer unit (104b) has a transparent wall (105) on its end, through which light emitted from the spherical medium-pressure UV lamp (106) may enter the reactor. The lamp (106) is coupled into the reactor by means of reflector (106a) which reflects the light in appropriate angles as for hitting the quartz wall in angles of incidence greater than the critical angle for achieving total internal reflection inside the reactor. The lines (106b) represent the typical path of light rays thus reflected. On its right hand the quartz tube (101) is opened to a fluid outlet unit (107a) which has a transparent window (107b) through which light exits the quartz tube toward a back reflector (109) which is designed to reflect the exiting light back into the reactor in appropriate angles for further achieving total internal reflection inside the quartz tube (101), now in the opposite direction as represented by arrow (109a).

Figure 11:
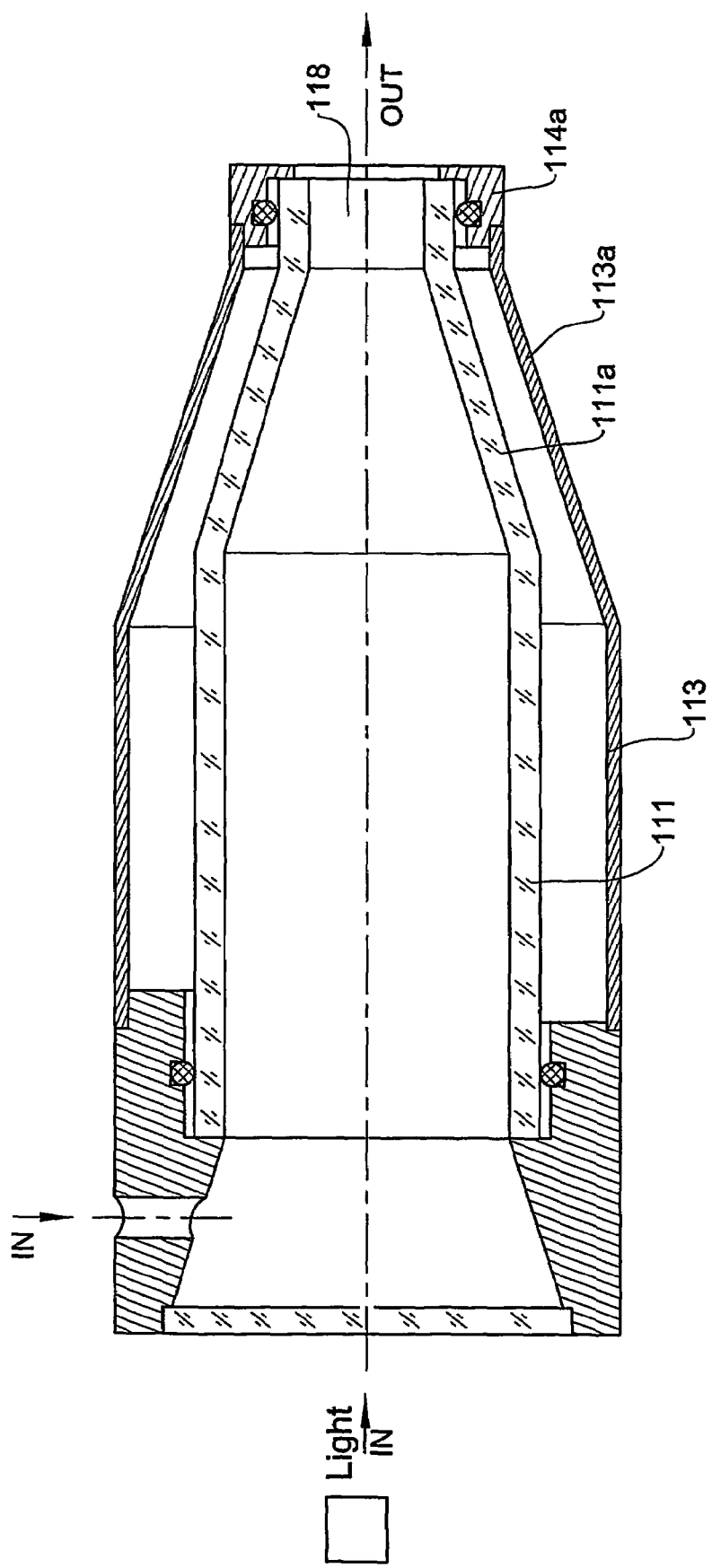
FIG. 11 illustrates a cross sectional view of a reactor embodiment according to the present invention having conical flow concentrator.

FIG. 11 illustrates a cross sectional view of a reactor embodiment according to the present invention having conical flow concentrator. This embodiment defers from that of FIG. 1 in that the quartz tube (111) of the present embodiment changes its form to a conical shape (111a) for having an outlet (118) of a smaller diameter comparing to the outlet (8) of the embodiment of FIG. 1. The protective metal sleeve (113) changes its form to a conical shape (113a) respectively, and the spacer (114a) has a reduced diameter, respectively. The conical portion of the reactor acts as an energy concentrator for increasing the light energy density towards the end of the reactor, where certain amounts of energy may have already been absorbed by the liquid.

Figure 12:
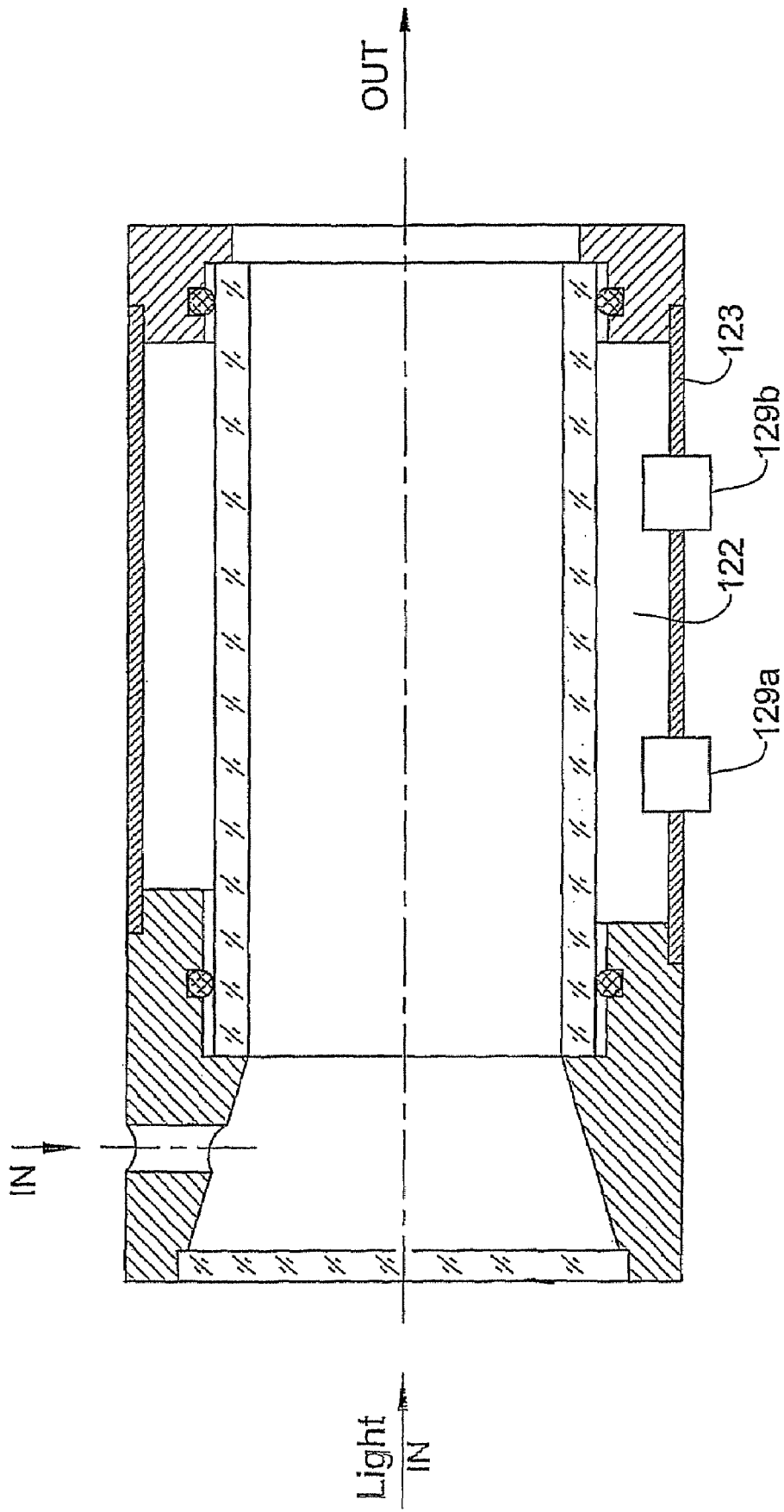
FIG. 12 illustrates a cross sectional view of a reactor according to the present invention having light monitoring detectors.

FIG. 12 illustrates a cross sectional view of a reactor according to the present invention having light monitoring detectors. This embodiment differs from that of FIG. 1, by further having light detectors (129a) and (129b) positioned in the air gap (122) and fixed to the wall of the protective sleeve (123). The detectors are used either to monitor the water quality (according to their turbidity degree which reflects on their transparency to light, thus on light residuals reaching the detectors (129a) (129b)) or to control the light energy by increasing intensity or by activating and inactivating light sources, according to the monitoring results.

Figure 13:
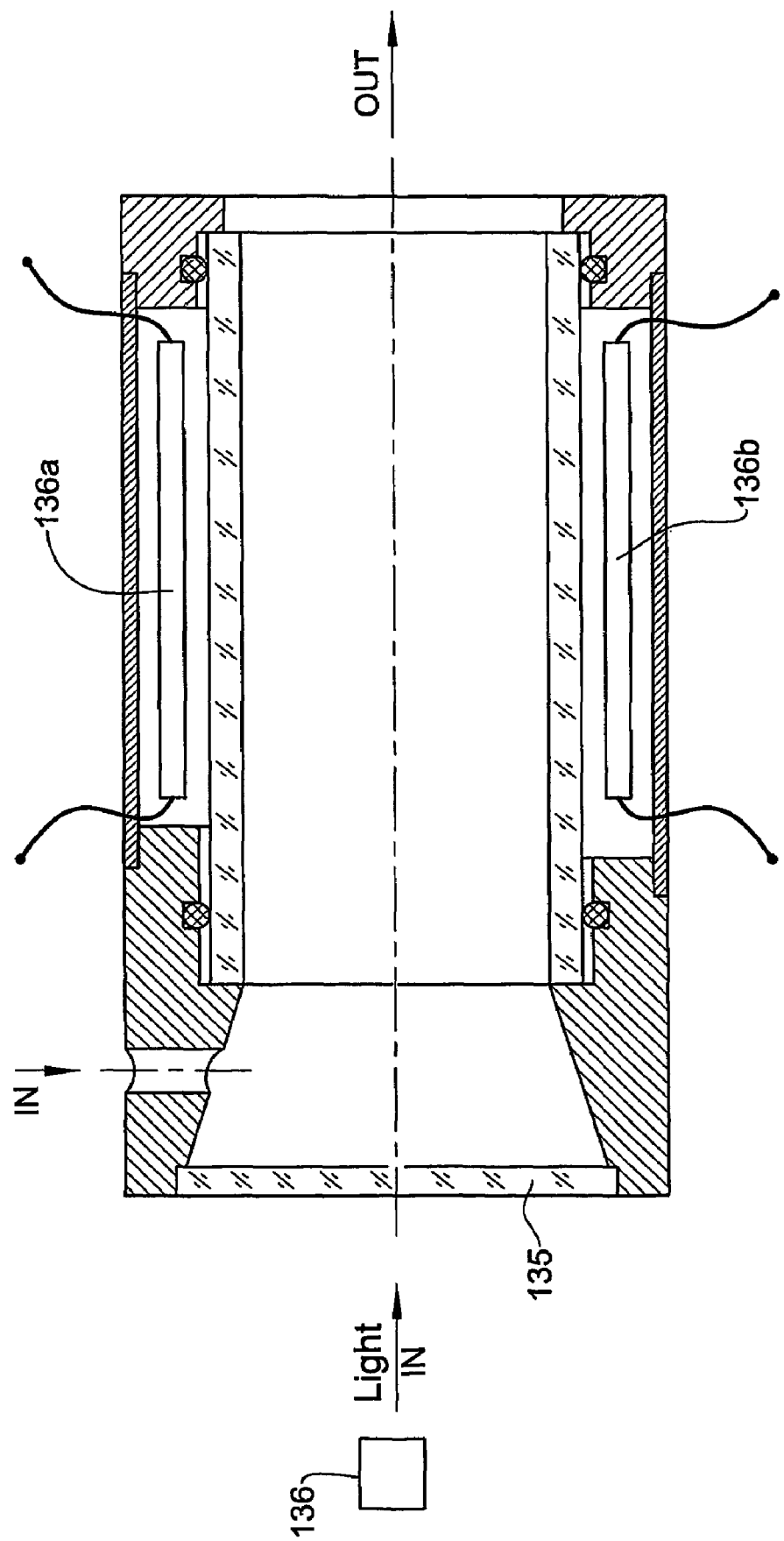
FIG. 13 illustrates a cross sectional view of a reactor according to the present invention having additional sources of light radiation positioned in the air gap between the reactor wall and its protective sleeve.

FIG. 13 illustrates a cross sectional view of a reactor according to the present invention having additional sources of light radiation, positioned in the air gap between the reactor wall and its protective sleeve. This is one example of how various light sources may be combined for the disinfection process according to the present invention, wherein the length of the reactor could be utilized for positioning longitudinally shaped UV light tubes (136a) (136b), in addition to any other light source (or sources) (136), positioned opposite the transparent end wall (135).

Figure 14:
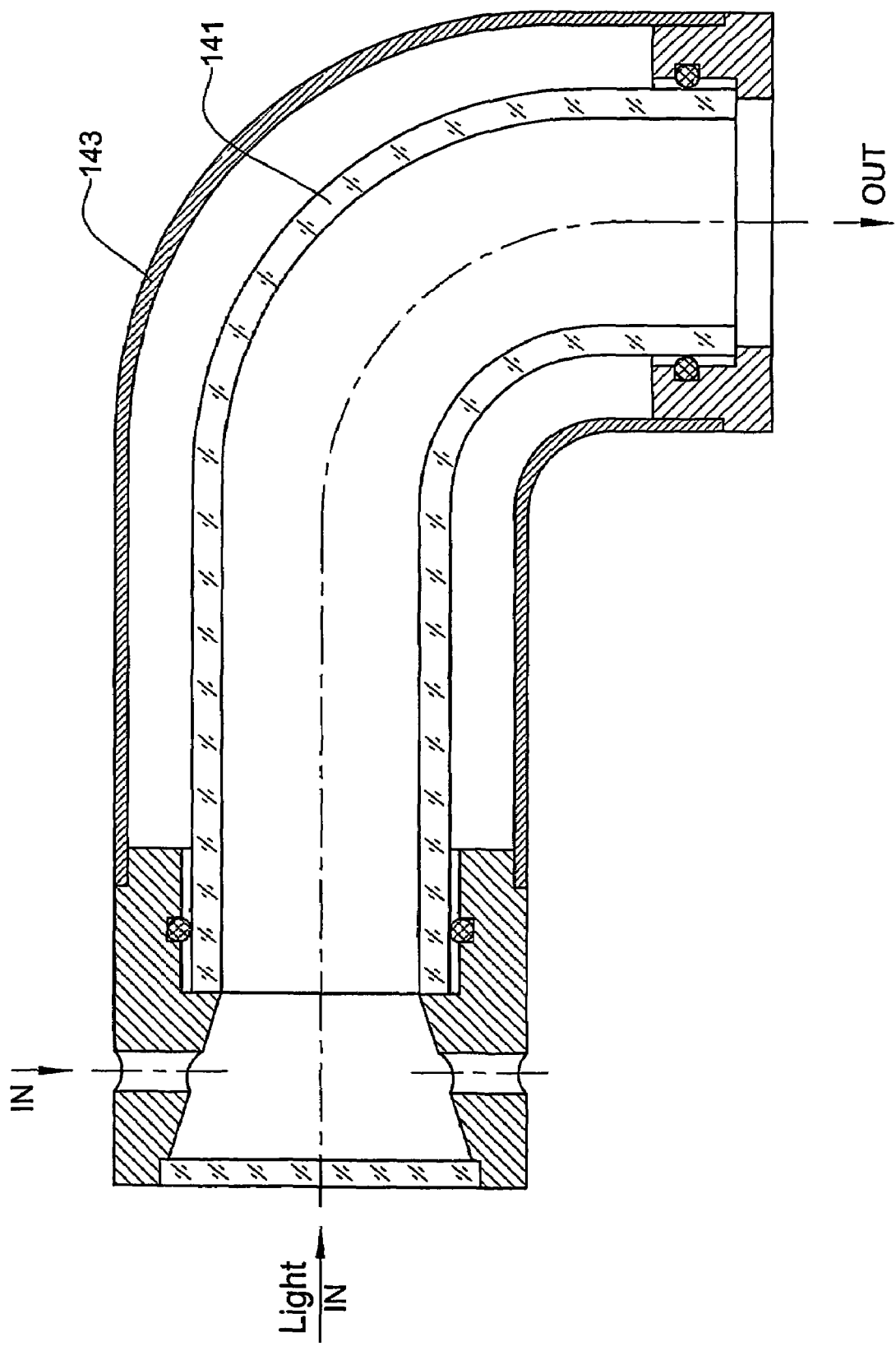
FIG. 14 illustrates a cross sectional view of a reactor according to the present invention having a bent portion.

FIG. 14 illustrates a cross sectional view of a reactor according to the present invention having a bent portion. This embodiment differs from that of FIG. 1, by having a bent quartz tube (141), and correspondingly bent metal sleeve (143) as a protective sleeve to the fragile quartz. The bending in the quartz tube is made in an appropriate radius (i.e. not less than required to assure that the (minimal possible angle of incidence will not be less than the critical angle for TIR) as to maintain the total internal reflection properties of the tube.

Figure 15:
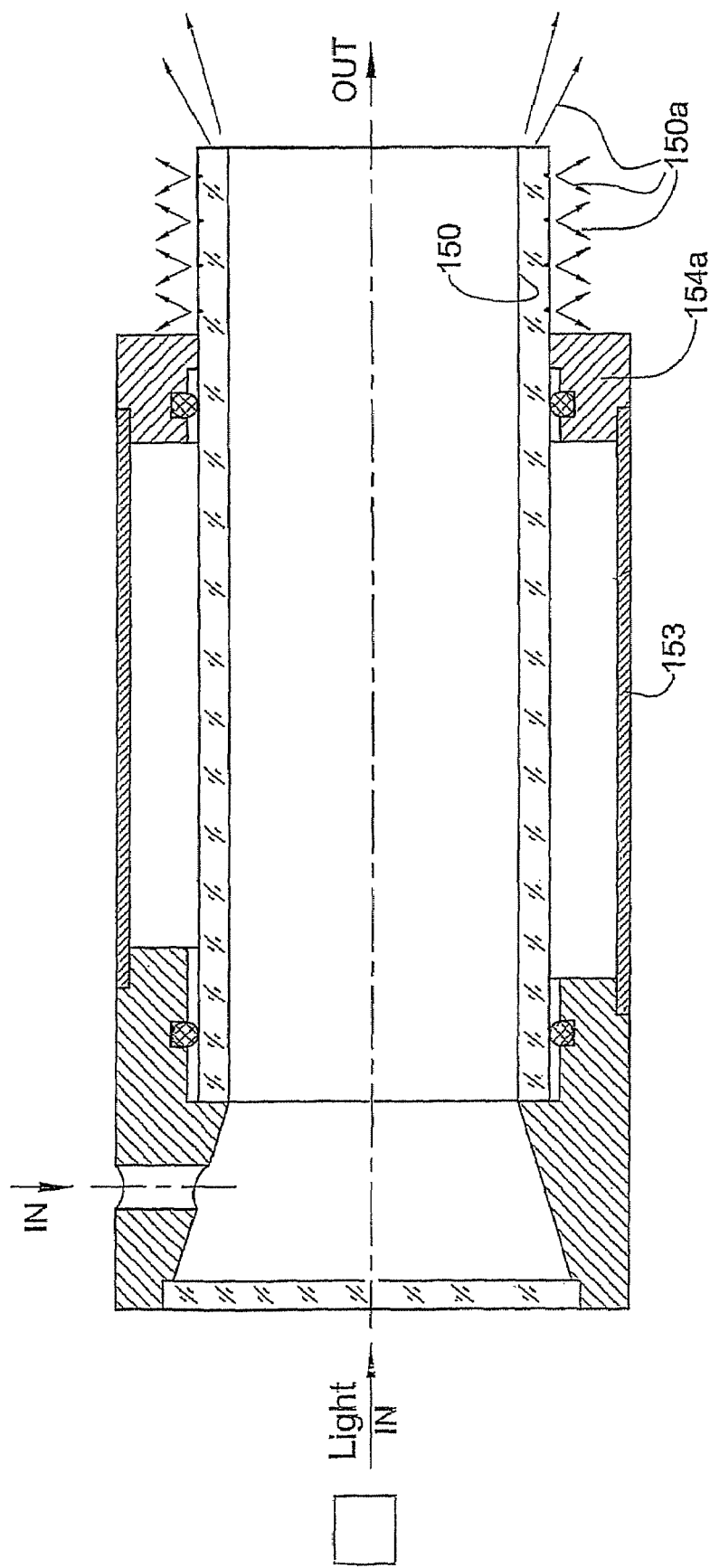
FIG. 15 illustrates a cross sectional view of a reactor according to the present invention ending with liquid launcher for acting as a disinfecting and washing device and/or as an aseptic filler device.

FIG. 15 illustrates a cross sectional view of a reactor according to the present invention ending with a quartz extension (150) protruding from the protective sleeve (153) and from the spacer (154a) for acting as a disinfecting and washing device and/or as an aseptic filler device, further to the in-line liquid treatment made inside the reactor. The edge of the tube could be prepared to have optical properties useful for the intended utilization of the emitted light. For example the edge could be formed convex or concave, and may be inclined inwardly or outwardly as an alternative to the depicted straight form. The surface of the quartz extension (150) may be etched or grooved (or as an alternative the quartz could be produced with internal impurities) for light diffusion as represented by arrows (150a), such that part of the light is emitted directly from the etched or grooved region to target surfaces (e.g. the inner walls of a bottle in which the right end of the reactor is lowered) for dry disinfection. Such dry disinfection could be performed by the reactor of this present embodiment prior to streaming the liquid through the reactor and continued thereafter during the filling procedure of the container to be filled with the in-line disinfected liquid.

Figure 15A:
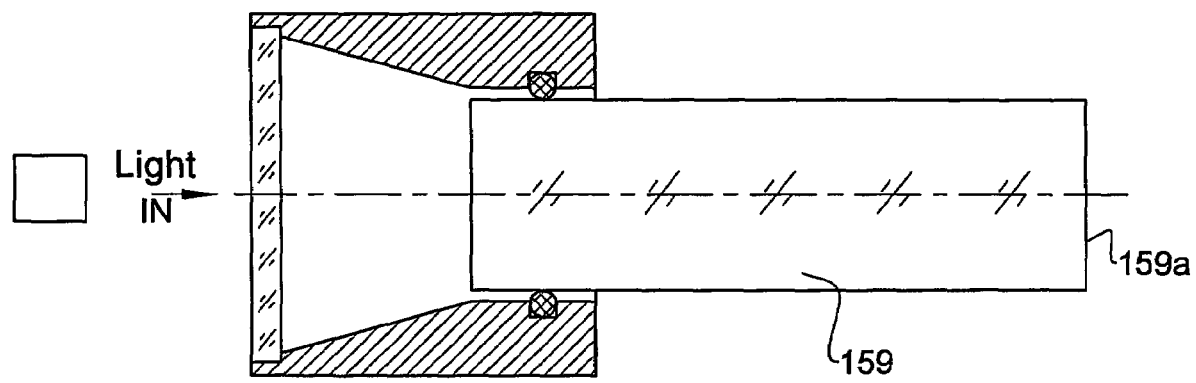
FIG. 15A illustrates a cross sectional view of a reactor embodiment according to the present invention ending with quartz rod for dry disinfection e.g. of pre-filled containers.

FIG. 15A illustrates a reactor embodiment wherein the tube has been replaced by a quartz rod (159), useful for dry disinfection e.g. of pre filled containers or bottles by inserting the rod through the container opening of a pre-filled container and irradiating it with UV germicidal light, in a similar manner to irradiating the reactor of the embodiment of FIG. 15. The rod (159) could be grooved or etched (or as an alternative the quartz could be produced with internal impurities) for homogenous light diffusion, and its right hand edge (159a) could be formed convex or concave, for respective diffusion or concentration of light, as an alternative to the depicted straight form. If so wished this present embodiment could be used for disinfecting filled containers by immersing the rod inside the liquid and irradiating the reactor and in turn the container liquid content.

Figure 15B:
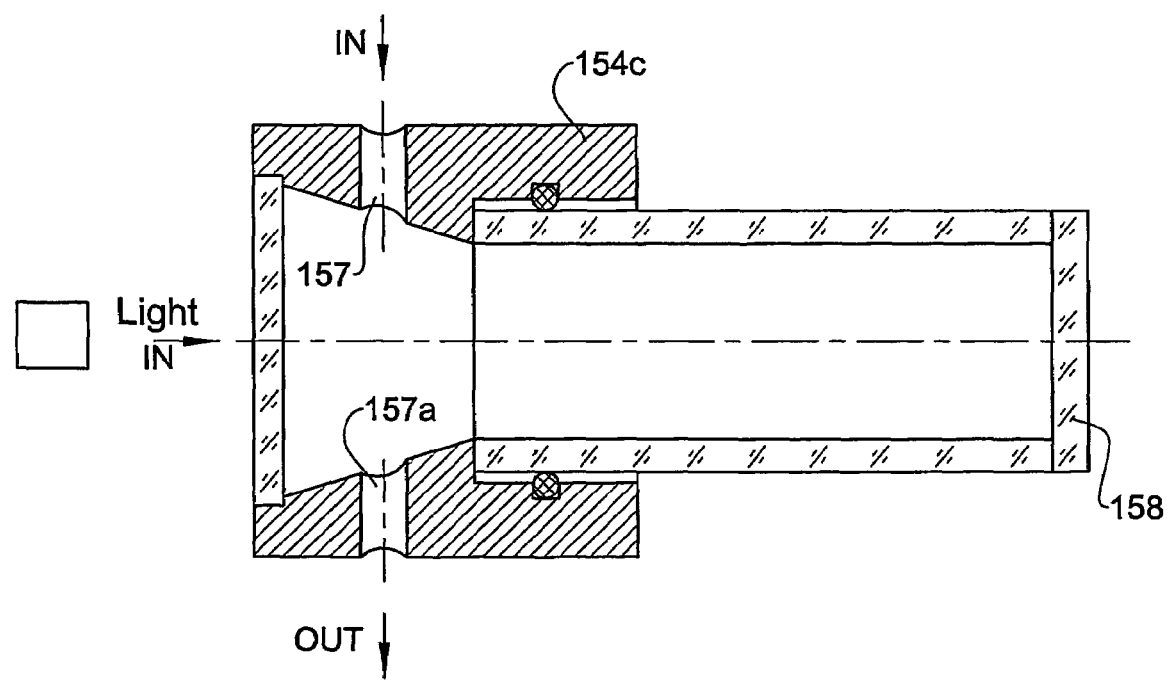
FIG. 15B illustrates a cross sectional view of a reactor embodiment according to the present invention ending with quartz tube for dry disinfection e.g. of pre-filled containers.

FIG. 15B illustrates a reactor embodiment with a tube closed at its right end with an end optic member (158), wherein the fluid inlet (157) and the fluid outlet (157a) are made in the spacer (154c), and wherein the tube could be utilized for dry cleaning similarly to the embodiment illustrated by FIG. 15A. The tube wall could be grooved or etched (or as an alternative the quartz could be produced with internal impurities) for homogenous light diffusion, and its right hand edge could be formed convex or concave, for respective diffusion or concentration of light, as an alternative to the depicted straight form.

Figure 16:
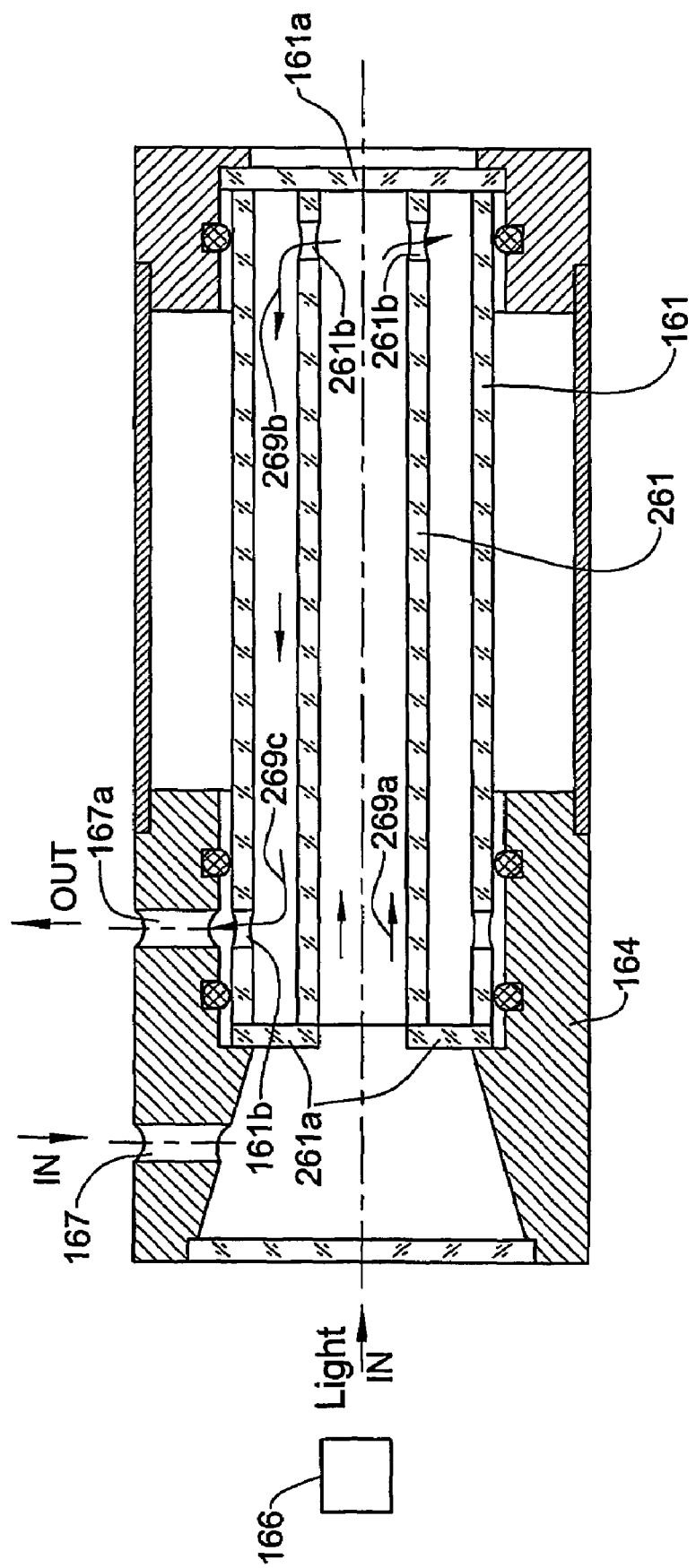
FIG. 16 illustrates a cross sectional view of a reactor according to the present invention having a quartz multi-core comprising two quartz tubes forming double length flow path.

FIG. 16 illustrates a cross sectional view of a reactor according to the present invention having a quartz multi-core comprising two quartz tubes forming double length flow path. The reactor according to this present embodiment is comprised of a first quartz tube (161) closed on its right hand by a back wall (161a). This wall may be transparent in order to allow positioning an external back reflector on the right hand of the reactor such that light exiting through the back wall (161a) could be reflected back from the external reflector into the reactor, or in order to allow positioning another light source to emit light radiation into the reactor in a direction opposite to that of the light originated by the light source (166) positioned on the left hand of the reactor. According to other variation of the present embodiment, the back wall (161a) is a reflector (or a mirror) by itself, reflecting back the light arriving to it from the light source (166). A second quartz tube (261) is positioned inside the quartz tube (161) participating with it the back wall (161a) which blocks the right hand of the quartz tube (261) as well. On the left hand of both the first and the second quartz tubes (161) and (261), respectively, a ring shaped wall (261a) blocks the right hand end of the gap formed between both tubes. The second (inner) quartz tube (261) is in fluid communication with the first (outer) quartz tube (161) through apertures (261b), thus allows for fluid flow from the fluid inlet (167) in the direction of the arrows (269a) (269b) (269c) to an outlet aperture (161b) made in the quartz wall of the first (outer) quartz tube (161) and communicated with the fluid outlet (167a) made in the spacer (164). This embodiment of reactor allows for duplicating the fluid flow path length through the a reactor of similar dimensions as that of the embodiment illustrated by FIG. 1. In a similar manner, additional inner quartz tubes of descending smaller diameters could be provided, one inside the other about a common longitudinal axis, to form a multi core reactor. The multi-core reactor could be designed with internal walls and fluid communication apertures to form one flow path of a length multiplied according to the number of tubes, or to form a plurality of separate flow paths, according the embodiment illustrated by FIG. 17 for a dual flow path.

Figure 17:
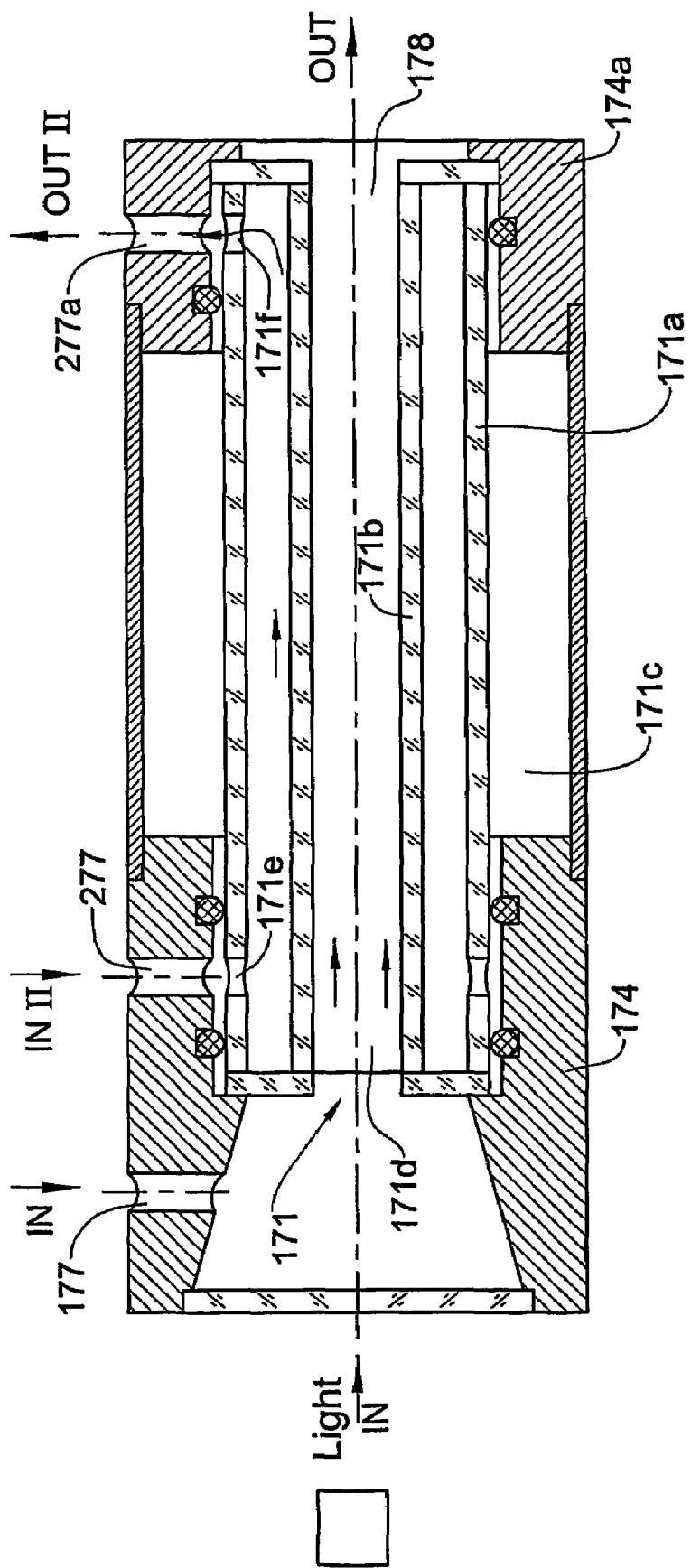
FIG. 17 illustrates a cross sectional view of a reactor according to the present invention having a quartz multi-core comprising two quartz tubes forming dual flow path.

FIG. 17 illustrates a cross sectional view of a reactor according to the present invention having a quartz multi-core comprising two quartz tubes forming dual flow path. The dual flow path according to this embodiment is provided by means of quartz made double wall cylinder (171), wherein the hollow space (171c) formed between its double walls (171a) and (171b) is isolated from the inner space (171d) of the double wall cylinder (171). Accordingly, a first flow path is provided through the inner space (171d) of the double wall cylinder (171) similarly to the flow path through the quartz tube (1) of the embodiment illustrated by FIG. 1. Fluid entering the reactor through fluid inlet (177) flow through the inner space (171d) of the double wall cylinder (171) until it exits the reactor through fluid outlet (178). In case a triple flow path reactor is required, or a reactor of a greater number of flow paths is required, additional quartz tubes of descending diameters should be added one inside another to form a multi wall cylinder of a plurality of separate inner spaces, wherein each inner space has its own fluid inlet and fluid outlet (the inlet and outlet of the inner walls can be piped to the outside through the external walls, or could be made at the right end and left end walls of the cylinder and piped directly to the spacer.

A second flow path is provided between a second fluid inlet (277) made in the wall of the spacer (174) and communicating with an inlet aperture (171e) made near the left end of the external quartz wall of the double wall cylinder (171), and between a second fluid outlet (277a) made in the wall of the right hand spacer (174a) and communicating with an outlet aperture (171f) made near the right end of the external quartz wall of the double wall cylinder (171). Although the two flow paths are separate, they are both irradiated from the same light source (or sources) due to internal reflection between the outer wall of the double wall cylinder (171) which crosses the inner wall of this quartz made cylinder, as well.

Figure 18:
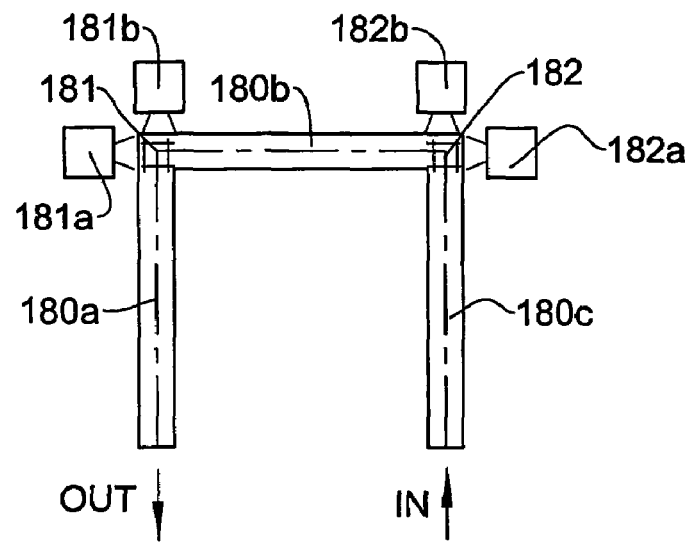
FIG. 18 illustrates multi reactor system architecture according to one of the embodiments of the present invention.

FIG. 18 illustrates multi reactor system architecture according to one of the embodiments of the present invention. This architecture involves reactor sections (180a) (180b) (180c) connected to one another in substantially right angle junctions (181) (182), wherein in each junction two light sources (181a) (181b), and (182a) (182b) are aligned with substantially right angle in between, to illuminate respectively into each of the reactor sections projected from the junction.

Figure 19:
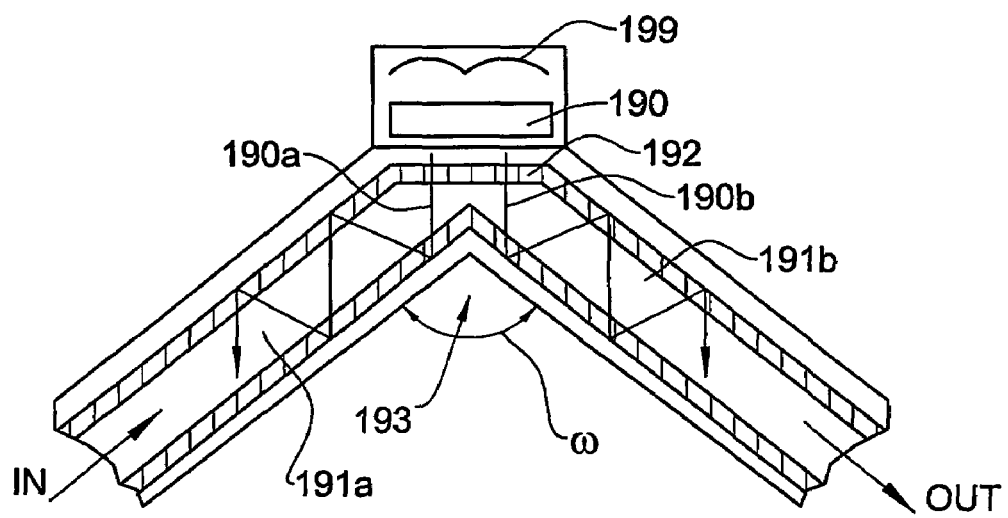
FIG. 19 illustrates multi reactor system architecture according to another embodiment of the present invention, especially useful for coupling rod type UV light sources.

FIG. 19 illustrates multi reactor system architecture according to another embodiment of the present invention, especially useful for coupling rod type UV light sources. According to this new architecture geometry, a microwave excited electrodeless UV plasma light tube (190) having an elongated form is positioned with its axis parallel to a substantially straight window (192) made in or being the wall of a junction (193) between two ends of reactor segments (191a) and (191b) oriented with an angle (w) between them both, the angle (w) is preferably as twice or more wider than the critical angle for total internal reflection in the pipe segments, such that the light emitted from a substantially one half of the UV light tube length enters the window (192) and irradiating (190a) the water accommodated in one of the pipe segments while the light emitted from substantially the second half of the UV light tube length enters the window (192) and irradiating the water accommodated in the second of the two pipe segments. The UV light tube (190) is equipped with a reflector (199) on its backside (the side of it which is opposite to the window (192)) which is designed to reflect light emitted from the backside of the light tube (190) or light reflected back from the window (192), back into the two reactor segments (191a) and (191b). The architecture of such two reactor segments will be referred to hereinafter also as "truncated A reactor". According to various preferred embodiments of the present embodiment the truncated A reactor architecture is designed as a modular system wherein a plurality of truncated A reactors could be connected one to another as a chain in order to provide an extended flow path reactor.

Figure 20:
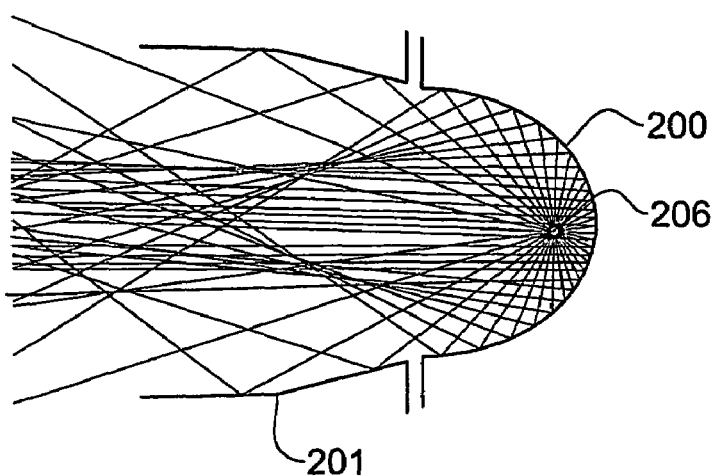
FIG. 20 illustrates a ray diagram of a reflector using for coupling light from A UV light source into reactors according to the present invention.

FIG. 20 illustrates a ray diagram of a reflector (200) using for coupling light from a UV light source (206) into reactors such as (201) according to the present invention. As can be appreciated, the light rays originated by the light source (206) in a peripheral manner, are reflected into the reactor (201) such that those of the light rays (represented by the depicted web of lies) who hit the reactor walls, hits in angles not greater than a predetermined angle, aimed to be the critical angle for total internal reflection of the light inside the reactor.

By utilizing the aforementioned embodiments or combinations thereof, the method according to the present invention allows for coupling a plurality of light engines into a hydro-optical geometry, lasers or lamps externally to the reactor while keeping angular orientation in modular format allowing the construction of wide myriad of reactors for sterilization and oxidation of inflow, inline water effluent, flow or for sterilization and decontamination of air, gases, surfaces or combinations.

The method according to the present invention provides for inline treatment and sterilization of air or gas inflow in cheese drying rooms, in diaries and milk production sites, in agro food production factories and in biomedical and pharmaceutical industries, in electronic industries, in green houses, in domestic air-conditioning systems, and in critical air or gas passages to human dwellings, shopping centers and malls, conference rooms, hotels, and in urban concentrations.

The reactors of the present invention, and in particular the truncated modular A shape could be used for inline treatment and sterilization of municipal drinking water, Ultra Pure Water (UPW) water for electronic industries, processed water for paper industries, aquaculture and fisheries, mineral, spring and bottled water, HOD (Home & Office Delivery services), for 5 gallon water jugs industry, for cooler industries, water reclamation, waste water or any combination thereof, water for baby foods and for washing food and medicine packaging and for germ free production of pharmaceutical products or for bio-security of domestic, industrial, commercial and public water systems, for desalination plants and for cooling towers or combinations.

In order to enhance the disinfection procedures according to the method of the present invention, the treatment of the fluids may further comprise adding small concentrations (e.g. 0.001%, or e.g. 0.01% or e.g. 0.1%, or e.g. 0.3%, or any other required concentration as known standards allow according to the particular case) of oxidizing agents, e.g. H2O2, to the flowing fluid, which could then be dissociated by the UV light energy, during the disinfection process, forming free radicals which may very effectively destroy various bacteria species of violent nature.

The treatment procedure may further comprise dissolving into the liquid being treated oxygen, or air, in order to create internal light diffuser comprising of a plurality of refractive index profiles within the liquid, useful for homogenous diffusion of light energy in the water.

The invention claimed is:

1. A liquid disinfection device comprising:
   a pipeline to hold flowing liquid to be treated with light radiation, the pipeline comprising walls made of light-transparent material and surrounded by air, a fluid inlet and a fluid outlet;
   a window adapted for the transmission of light into the pipeline, wherein the liquid flows in a space between the window and the pipeline;
   a light source external to said pipeline to generate light to be transmitted through the window into the flowing liquid within the pipeline; and
   a reflector to reflect light generated by said light source through said window into the flowing liquid within the pipeline, wherein the reflected light strikes the walls of the pipeline at angles of incidence greater than a critical angle for total internal reflection to enable the total internal reflection.

2. The liquid disinfection device of claim 1, wherein the walls of the pipeline are made of quartz.

3. The liquid disinfection device of claim 1, wherein the pipeline is positioned inside a protective sleeve with an air gap in between.

4. The liquid disinfection device of claim 1, wherein the window is provided with an optical filter to block light of a predetermined wavelength spectrum from entering the pipeline.

5. The liquid disinfection device of claim 1, further comprising one or more light detectors to detect light energy at one or more predetermined regions of the pipeline, and a controller to control one or more disinfection-related parameters of said disinfection device based on the detected light energy.

6. The liquid disinfection device of claim 1, further comprises at least one additional pipeline made of light-transparent material wherein the pipelines are of descending diameters and are positioned one inside another with gaps in between.

7. The liquid disinfection device of claim 1, wherein the fluid outlet is formed as a filling nozzle in a liquid filling apparatus.

8. The liquid disinfection device of claim 1, wherein the fluid outlet is formed as a water launcher in a washing apparatus.

9. The liquid disinfection device of claim 1, wherein said window has a surface area equal to or bigger than an inner diameter of said pipeline between said inlet and said outlet.

10. The liquid disinfection device of claim 1, wherein said window is located such that said light enters said pipeline at a direction corresponding to a flow direction of said liquid between said inlet and said outlet.

11. In a domestic water supply system, the liquid disinfection device according to claim 1, further comprising a faucet adapted to be activated by a domestic user, in liquid communication with the fluid outlet.

12. The liquid disinfection device of claim 1, wherein the light source is selected from the group consisting of a UV plasma lamp, a UV laser, a pulsed UV lamp, and a mercury lamp.

13. A method for disinfecting liquids, the method comprising:
- accommodating flowing liquid to be disinfected in a pipeline comprising walls made of a liqht-transparent material, and the surrounding outside the wall is of a refractive index lower then that of the liquid;
- positioning a light-transparent window externally to the pipeline leaving a space between said window and said pipeline for liquid to flow;
- generating liqht radiation externally to said pipeline to be transmitted through said window into the flowinq liquid within the pipeline; and
- reflecting, with a reflector, said light radiation into said liquid flowinq through the pipeline such that light is transmitted through the window into the liquid, and such that a major portion of said light strikes the walls of the pipeline at angles of incidence greater than a critical angle for total internal reflection to enable the total internal reflection.

14. The method according to claim 13, wherein the transparent material is quartz.

15. The method according to claim 13, wherein the liquid is water or other liquid transparent to certain wave lengths of the light radiation.

16. The method according to claim 15 comprising launching the water from the outlet to form a free flow water jet with light radiation locked in total internal reflection within the jet.

17. The method according to claim 16, further comprising washing a surface or a container with the free flow jet.

18. The method according to claim 16, further comprising filling a bottle or a container with the free flow jet.

19. The method according to claim 18 comprising simultaneously evacuating the air rejected from the container by the liquid being filled, and suctioning it into another device reactor or into a second flow channel in the same device in which the liquid is irradiated, for irradiating the air.

20. The method according to claim 18, further comprising dry-disinfecting the containers to be filled by means of quartz rod inserted into the container opening and irradiating it with UV emitted from the rod.

21. The method according to claim 16, further comprising dissolving into the liquid oxidizing agents, air, or gas, in order to enhance the disinfection process.

\* \* \* \* \*